United States Patent
Crook et al.

(10) Patent No.: US 7,485,146 B1
(45) Date of Patent: Feb. 3, 2009

(54) TOTAL DISC REPLACEMENT SYSTEM AND RELATED METHODS

(75) Inventors: David Crook, San Diego, CA (US); G. Bryan Cornwall, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 293 days.

(21) Appl. No.: 11/075,902

(22) Filed: Mar. 8, 2005

Related U.S. Application Data

(60) Provisional application No. 60/571,551, filed on May 13, 2004, provisional application No. 60/551,621, filed on Mar. 8, 2004.

(51) Int. Cl.
*A61F 2/44* (2006.01)

(52) U.S. Cl. .................................................. 623/17.15

(58) Field of Classification Search ... 623/17.11–17.16; 606/61
See application file for complete search history.

(56) References Cited

U.S. PATENT DOCUMENTS

| | | | |
|---|---|---|---|
| 5,171,282 A * | 12/1992 | Pequignot | 623/20.35 |
| 5,425,773 A * | 6/1995 | Boyd et al. | 623/17.15 |
| 2003/0204261 A1 * | 10/2003 | Eisermann et al. | 623/17.14 |
| 2004/0133278 A1 * | 7/2004 | Marino et al. | 623/17.14 |
| 2004/0133281 A1 * | 7/2004 | Khandkar et al. | 623/17.16 |
| 2004/0143332 A1 * | 7/2004 | Krueger et al. | 623/17.14 |
| 2005/0149194 A1 * | 7/2005 | Ahlgren | 623/17.11 |
| 2005/0154468 A1 * | 7/2005 | Rivin | 623/17.16 |
| 2005/0159818 A1 * | 7/2005 | Blain | 623/17.15 |
| 2005/0165485 A1 * | 7/2005 | Trieu | 623/17.13 |
| 2006/0009850 A1 * | 1/2006 | Frigg et al. | 623/17.13 |

FOREIGN PATENT DOCUMENTS

WO    WO 2004002291 A2 *    1/2004

\* cited by examiner

*Primary Examiner*—Eduardo C Robert
*Assistant Examiner*—Nicholas Woodall
(74) *Attorney, Agent, or Firm*—Jay B. Bell

(57) ABSTRACT

A total disc replacement (TDR) system for use in the spine and related methods, involving a first anchor plate having a first surface for engaging a first vertebra and a second surface including a semi-cylindrical surface, a second anchor plate having a first surface for engaging a second vertebra and a second surface including a semi-cylindrical surface, a pair of intradiscal liners, each having a first semi-cylindrical surface for engaging with said anchor plates and a second semi-cylindrical surface for engaging with an intradiscal element, and an intradiscal element including a first articular surface having a generally arcuate cross-section for articulating with said first intradiscal liner, and a second articular surface having a generally arcuate cross-section for articulating with said second intradiscal liner.

21 Claims, 16 Drawing Sheets

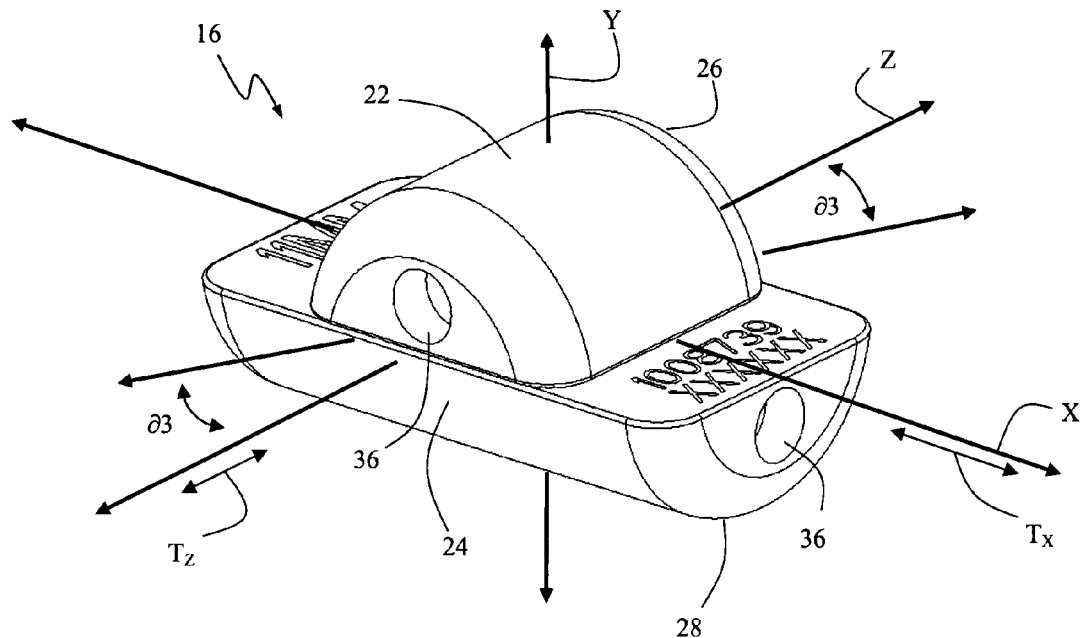
FIG. 6
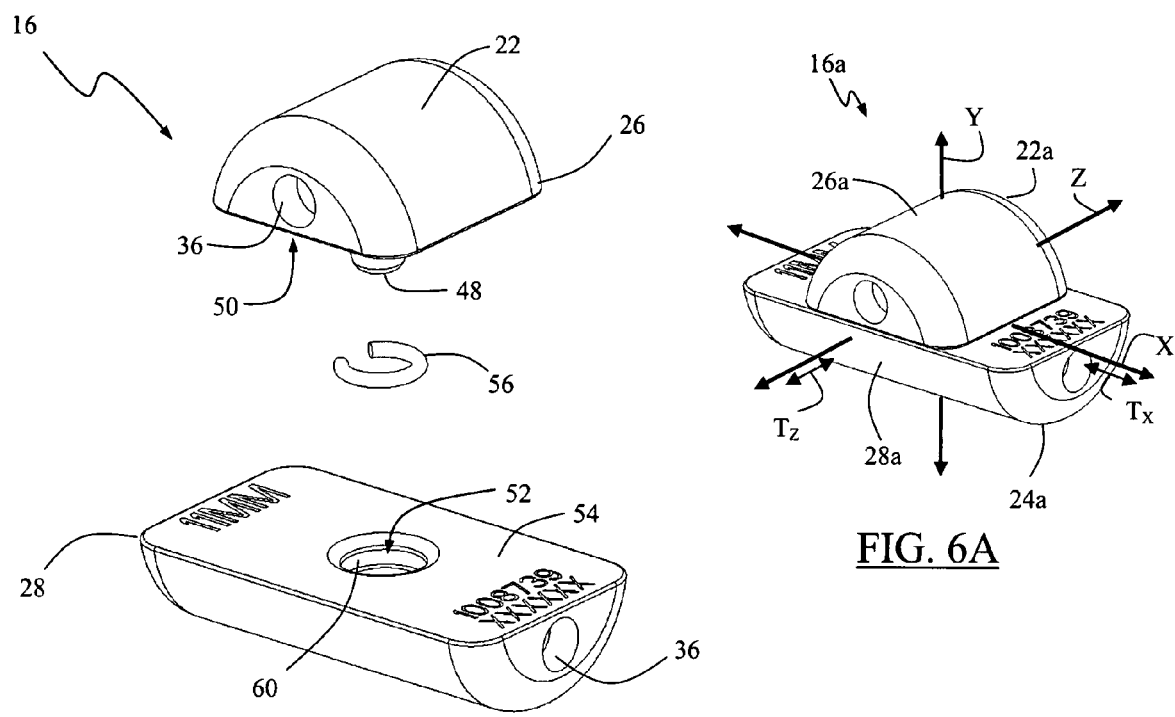
FIG. 7
FIG. 6A

TOTAL DISC REPLACEMENT SYSTEM AND RELATED METHODS

CROSS REFERENCES TO RELATED APPLICATIONS

The present application is a nonprovisional patent application claiming benefit under 35 U.S.C. § 119(e) from U.S. Provisional Application Ser. No. 60/551,621, filed on Mar. 8, 2004, and U.S. Provisional Application Ser. No. 60/571,551, filed on May 13, 2004, the entire contents of which are hereby expressly incorporated by reference into this disclosure as if set forth fully herein.

BACKGROUND OF THE INVENTION

I. Field of the Invention

The present invention relates generally to spinal surgery and, more particularly, to total disc replacement systems and related methods.

II. Discussion of the Prior Art

In recent years, the area of total disc replacement has experienced proliferated growth and attention from the medical community. Known total disc replacement devices generally require some form of articulation or inherent flexibility in the device to permit a spine having the device to maintain its natural posture and range of motion as much as possible. Such devices typically include between 2 and 4 separate components constructed from any number of materials, such as plastic, rubber, metal, ceramic and alloys. Generally speaking, these components include a pair of anchor plates for engagement with opposed vertebral body endplates and one or more internal components for simulating the intervertebral disc.

Known total disc replacement systems suffer disadvantages including the dislocation of the anchor plates from the vertebral end plates, over-distraction of the vertebral endplates during introduction, particulate wear and debris of the component parts, and a lack of conformity between the anchor plates and the internal components during use. The present invention is directed at overcoming, or at least reducing the effects of, one or more of the problems set forth above.

SUMMARY OF THE INVENTION

The present invention solves the above-identified drawbacks with the prior art by providing a total disc replacement system including a pair of anchor plates, a pair of intradiscal troughs, or liners, and an intradiscal element. The first anchor plate has a first surface for engaging a first vertebra and a second surface including a semi-cylindrical surface. The second anchor plate has a first surface for engaging a second vertebra and a second surface including a semi-cylindrical surface. The intradiscal liners each have a first semi-cylindrical surface for engaging with the first and second anchor plates, and a second semi-cylindrical articular surface for engaging with the intradiscal element. The intradiscal element includes a first articular surface having a generally arcuate cross-section for articulating with the semi-cylindrical articular surface of the first intradiscal liner, and a second articular surface having a generally arcuate cross-section for articulating with the semi-cylindrical articular surface of the second intradiscal liner. As used herein, the term "semi-cylindrical" is defined to mean any cylindrical shape which has a cross-section of a full circle or less than a full circle.

The semi-cylindrical surfaces of the intradiscal liners are dimensioned in such a way to fit snugly with the semi-cylindrical surfaces of the first and second anchor plates such that the intradiscal liners do not move (either by rotation or lateral translation) relative to the anchor plates. Referring to the intradiscal element, the first articular surface is dimensioned to articulate with the semi-cylindrical articular surface of the first intradiscal liner, and by extension, the first anchor plate such that the first anchor plate may rotate relative to the intradiscal element about a first axis (e.g. Z-axis), as well as translate relative to the intradiscal element in either direction along the first axis. The second articular surface is dimensioned to articulate with the semi-cylindrical articular surface of the second intradiscal liner, and by extension, the second anchor plate such that the second anchor plate may rotate relative to the intradiscal element about a second axis (e.g., X-axis), as well as translate relative to the intradiscal element in either direction along the second axis. In this fashion, rotation about the first axis will always occur at the same location along the first anchor plate and rotation about the second axis will always occur at the same location along the second anchor plate. In an optional configuration, the intradiscal element may (by way of example only) comprise a first intradiscal element rotatably coupled to a second intradiscal element, which allows relative rotation along a third axis (e.g., Y-axis). In use, then, the TDR system of the present invention provides rotation along three distinct axes (e.g., X, Y, Z) and translation along two distinct axes (e.g., X and Z).

The semi-cylindrical surface of the first and/or second anchor plates and the first and/or second intradiscal liners may be generally concave and/or generally convex. The generally arcuate cross-sections of the first and/or second articular surfaces of the intradiscal element may be generally concave and/or convex. The second surface of the first and/or second anchor plates may include a ramped portion to facilitate the introduction of the intradiscal element into articulating engagement with the semi-cylindrical articular surfaces of the first and second anchor plates. The intradiscal element may be prevented from translating relative to the first and/or second anchor plates.

The first and second anchor plates may each include a plurality of anchor elements for anchoring into adjacent vertebrae. The anchor elements may include a plurality of protrusions having a triangular shaped cross-section. In one aspect, the anchor elements are oriented such that the first and second anchor plates may be introduced in a generally lateral approach relative to the first and second vertebrae. In another aspect, the anchor elements are oriented such that the first and second anchor plates may be introduced in a generally anterior approach relative to the first and second vertebrae.

The intradiscal element may take any number of different forms. In one aspect, the intradiscal element is generally spherical and may be provided as a single generally spherical member or at least two semi-spherical members coupled together. In another aspect, the intradiscal element may include at least one generally semi-cylindrical articular surface for articulating with the semi-cylindrical articular surface of the first and/or second anchor plate. In this embodiment, the intradiscal element may be provided as a unitary member and/or may comprise a first intradiscal element rotatably coupled to a second intradiscal element via (by way of example only) a post.

The first anchor plate, second anchor plate, and/or intradiscal element may be provided with at least one lumen for engagement with an insertion tool.

The first anchor plate, second anchor plate, first intradiscal liner, second intradiscal liner, and/or intradiscal element may be constructed from metal, ceramic, polymer, and/or any combination thereof.

An alternative embodiment of the total disc replacement system of the present invention is provided including a pair of anchor plates, two pairs of intradiscal liners, and an intradiscal element. The first anchor plate has a first surface for engaging a first vertebra and a second surface opposite the first surface including a cutout region for engaging an intradiscal element. The second anchor plate has a first surface for engaging a second vertebra and a second surface opposite the first surface including a cutout region for engaging an intradiscal element. The first pair of intradiscal liners each have a first surface for engaging with the first anchor plate, a second generally planar surface, and a semi-cylindrical articular surface for engaging with the intradiscal element. The second pair of intradiscal liners each have a first surface for engaging with the second anchor plate, a second generally planar surface, and a semi-cylindrical articular surface for engaging with the intradiscal element. The intradiscal element includes at least a first and a second articular surface, each having a generally arcuate cross-section for articulating with the semi-cylindrical articular surfaces of the first and second pairs of intradiscal liners. In an optional lower profile configuration of the TDR system described herein, the intradiscal element may also contain a pair of opposing generally planar surfaces for engaging the first and second anchor plates. In such a configuration, the first and second articular surfaces may be interrupted by said generally planar surfaces, resulting in a first and second pair of articular surfaces. As used herein, the term "semi-cylindrical" is defined to mean any cylindrical shape which has a cross-section of a full circle or less than a full circle.

The first surface of the first pair of intradiscal liners are dimensioned in such a way to fit snugly within the cutout region of the first anchor plate such that the intradiscal liners do not move (either by rotation or lateral translation) relative to the anchor plate. Similarly, the first surface of the second pair of intradiscal liners are dimensioned in such a way to fit snugly within the cutout region of the second anchor plate such that the intradiscal liners do not move (either by rotation or lateral translation) relative to the anchor plate.

Referring to the intradiscal element, the first pair of articular surfaces are dimensioned to articulate with the semi-cylindrical articular surfaces of the first pair of intradiscal liners, and by extension the first anchor plate, such that the first anchor plate may rotate relative to the intradiscal element about a first axis (e.g. Z-axis), as well as translate relative to the intradiscal element in either direction along the first axis. The second pair of articular surfaces are dimensioned to articulate with the semi-cylindrical articular surfaces of the second pair of intradiscal liners, and by extension the second anchor plate, such that the second anchor plate may rotate relative to the intradiscal element about a second axis (e.g., X-axis), as well as translate relative to the intradiscal element in either direction along the second axis. In this fashion, rotation about the first axis will always occur at the same location along the first anchor plate and rotation about the second axis will always occur at the same location along the second anchor plate. In an optional configuration, the intradiscal element may (by way of example only) comprise a first intradiscal pivot rotatably coupled to a second intradiscal pivot, which allows relative rotation along a third axis (e.g., Y-axis). In such a configuration, the first intradiscal pivot may include a first pair of articulating surfaces and a first generally planar surface, and the second intradiscal pivot may include a second pair of articulating surfaces and a generally planar surface. In use, then, the TDR system of the present invention provides rotation along three distinct axes (e.g., X, Y, Z) and translation along two distinct axes (e.g., X and Z).

The semi-cylindrical articular surfaces of the first and/or second pairs of intradiscal liners and the first and/or second intradiscal pivots may be generally concave and/or generally convex. The second surface of the first and/or second anchor plates may include a ramped portion to facilitate the introduction of the intradiscal element into articulating engagement with the semi-cylindrical articular surfaces of the first and second pairs of intradiscal liners. The intradiscal element may be prevented from translating relative to the first and/or second anchor plates by any suitable method, such as (by way of example only) by including one or more obstructions along the first and/or second intradiscal liners and/or cutout regions or by the introduction of a suitable adhesive substance.

The first and second anchor plates may each include a plurality of anchor elements for anchoring the TDR device of the present invention into adjacent vertebrae. The anchor elements may include a plurality of protrusions having a cross-section having any number of suitable shapes, including but not limited to generally triangular. In one aspect, the anchor elements may be oriented such that the first and second anchor plates may be introduced in a generally anterior approach relative to the first and second vertebrae. In another aspect, the anchor elements may be oriented such that the first and second anchor plates may be introduced in a generally lateral approach relative to the first and second vertebrae.

The intradiscal element may take any number of different forms. In one aspect, the intradiscal element may be provided as a single generally spherical member or at least two semispherical members coupled together. In another aspect, intradiscal element may include at least one generally semi-cylindrical articular surface for articulating with the semi-cylindrical articular surface of the first and/or second pair of intradiscal liners. In this embodiment, the intradiscal element may be provided as a unitary member and/or may comprise a first intradiscal pivot rotatably coupled to a second intradiscal pivot via (by way of example only) a post. In yet another aspect, the intradiscal element may include a pair of opposing generally planar surfaces in order to reduce the overall profile of the total disc replacement system of the present invention.

The first anchor plate, second anchor plate, intradiscal liners, and/or intradiscal element may be provided with at least one lumen, groove, and/or other mechanism for engagement with an insertion tool.

The first anchor plate, second anchor plate, first pair of intradiscal liners, second pair of intradiscal liners, and/or intradiscal element may be constructed from any number of suitable materials, including but not limited to metal, ceramic, polymer, and/or any combination thereof.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 6 is a perspective view of an intradiscal element forming part of the total disc replacement system of FIG. 1;

FIG. 6A is a perspective view of an alternative embodiment of an intradiscal element forming part of the total disc replacement system of FIG. 1;

FIG. 7 is an exploded perspective view of the intradiscal element of FIG. 6;

DESCRIPTION OF THE PREFERRED EMBODIMENT

Figure 1:
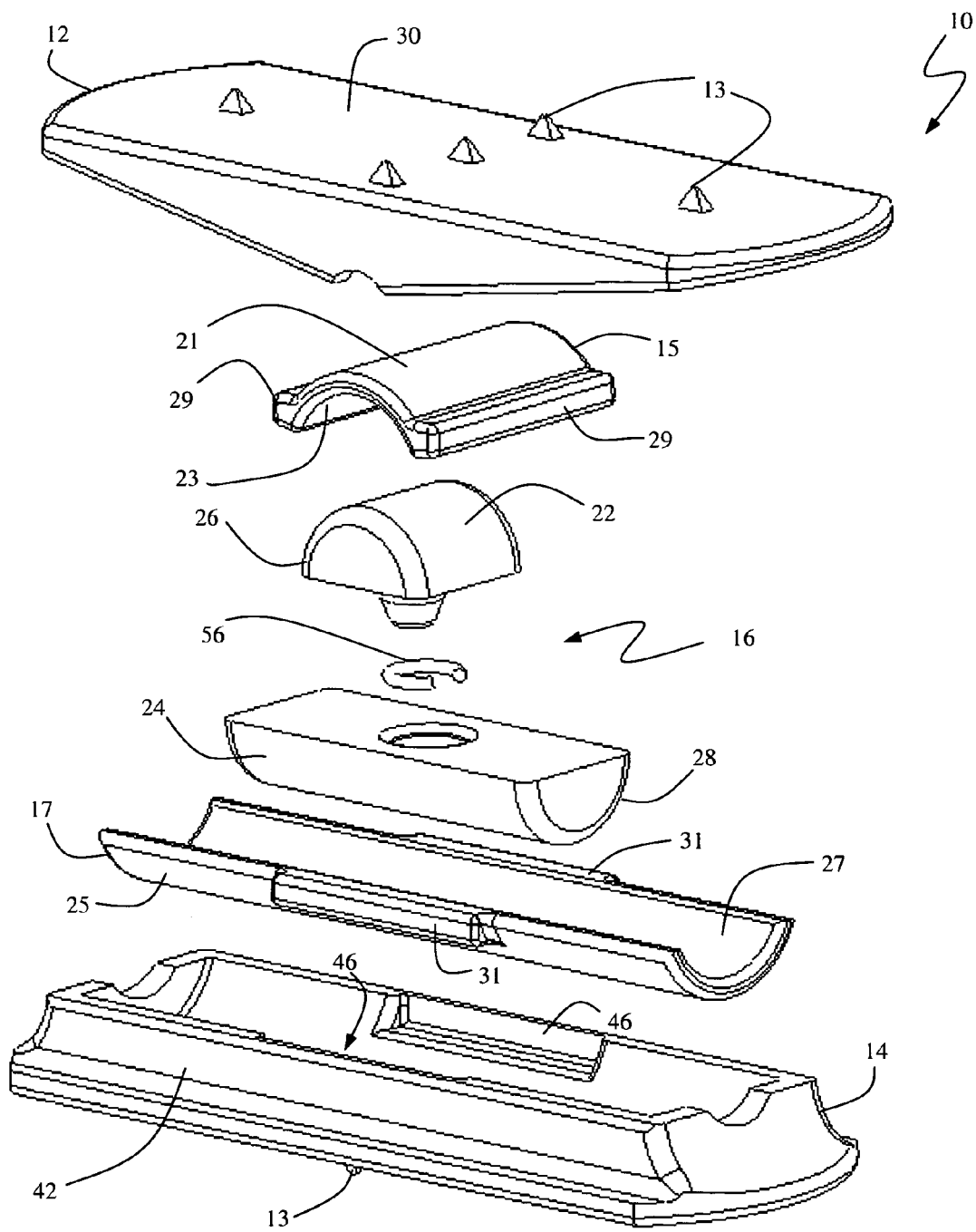
FIG. 1 is an exploded perspective view of a total disc replacement system according to a first embodiment of the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The total disc replacement system and related methods disclosed herein boasts a variety of inventive features and components that warrant patent protection, both individually and in combination.

FIGS. 1-5 illustrate a total disc replacement (TDR) system 10 according to a first embodiment of the present invention. The TDR system 10 includes a first anchor plate 12, a second anchor plate 14, a pair of intradiscal troughs or liners 15, 17, and an intradiscal element 16. Each anchor plate 12 and 14 is equipped with a plurality of anchor elements 13 and a semi-cylindrical surface 18, 20, respectively. The first intradiscal liner 15 includes a first surface 21 and a second surface 23, each having a generally arcuate cross-section. The first surface 21 is dimensioned to fit into the semi-cylindrical surface 18 of the first anchor plate 12, allowing the first intradiscal liner 15 to form a protective barrier between intradiscal element 16 and first anchor plate 12, thereby reducing wear. The second intradiscal liner 17 includes a first surface 25 and a second surface 27, each having a generally arcuate cross-section. The first surface 25 is dimensioned to fit into the semi-cylindrical surface 20 of the second anchor plate 14, allowing the second intradiscal liner 17 to form a protective barrier between intradiscal element 16 and second anchor plate 14, thereby reducing wear.

The intradiscal element 16 includes a first articular surface 22 and a second articular surface 24, each having a generally arcuate cross-section. The first articular surface 22 is dimensioned to articulate with the second surface 23 of the first intradiscal liner 15 such that, by extension, the first anchor plate 12 may rotate relative to the intradiscal element 16 about the Z-axis (FIGS. 6 & 10), as well as translate relative to the intradiscal element 16 in either direction along the Z-axis (denoted as line "$T_Z$"). The second articular surface 24 is dimensioned to articulate with the second surface 27 of the second intradiscal liner 17 such that, by extension, the second anchor plate 14 may rotate relative to the intradiscal element 16 about the X-axis (FIGS. 6 & 9), as well as translate relative to the intradiscal element 16 in either direction along the X-axis (denoted as line "$T_X$"). In this fashion, rotation about the Z-axis will always occur at the same location along the first anchor plate 12 and rotation about the X-axis will always occur at the same location along the second anchor plate 14. The intradiscal element 16 may optionally (by way of example only) comprise a first intradiscal element 26 rotatably coupled to a second intradiscal element 28, which allows relative rotation along the Y-axis. In use, then, the TDR system 10 of this first embodiment provides rotation along three distinct axes (X, Y, Z) and translation along two distinct axes (X and Z).

When used within the lumbar spine, for example, it may be desirable to configure the second anchor plate 14 such that the semi-cylindrical surface 20 (and hence X-axis) is located within the posterior one-third of the disc space (and generally within the frontal plane of the patient) to approximate the axis of rotation of the natural spine during flexion and extension. It may similarly be desirable to configure the first anchor plate 12 such that the semi-cylindrical surface 18 (and hence Z-axis) is located at the approximate center of the disc space (and generally within the sagittal plane of the patient) to approximate the axis of rotation of the natural spine during lateral bending. Although described by way of example in this configuration, it will be appreciated that the relative position of the semi-cylindrical articular surfaces 18, 20 may be altered in any number of different fashions depending upon the vertebral level (i.e. cervical, thoracic, and/or lumbar) as well as the directional approach employed to place the TDR system 10 into a disc space (e.g., lateral, anterior, postero-lateral, antero-lateral). Moreover, it will be appreciated that the TDR system 10 may be introduced into a disc space in the orientation shown (with the first anchor plate 12 "above" the second anchor plate 14 such that the anchor elements 13 are to be disposed within a respective "upper" and "lower" vertebral level within the patient) or vice versa.

Figure 2:
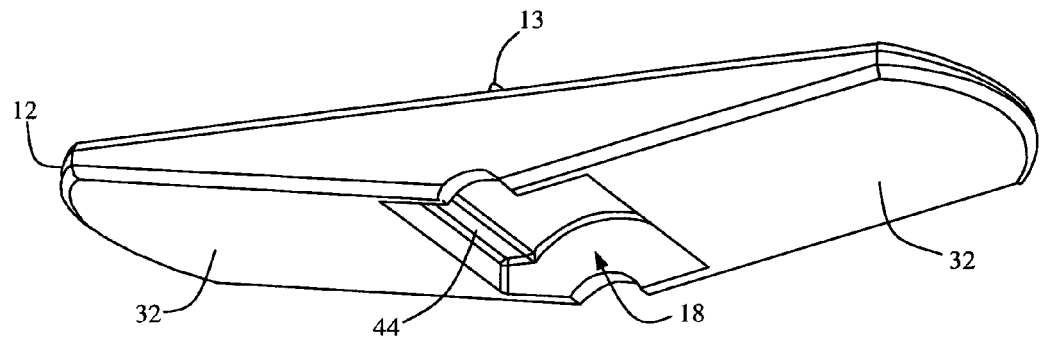
FIG. 2 is a perspective view of a first anchor plate forming part of the total disc replacement system of FIG. 1.
Figure 3:
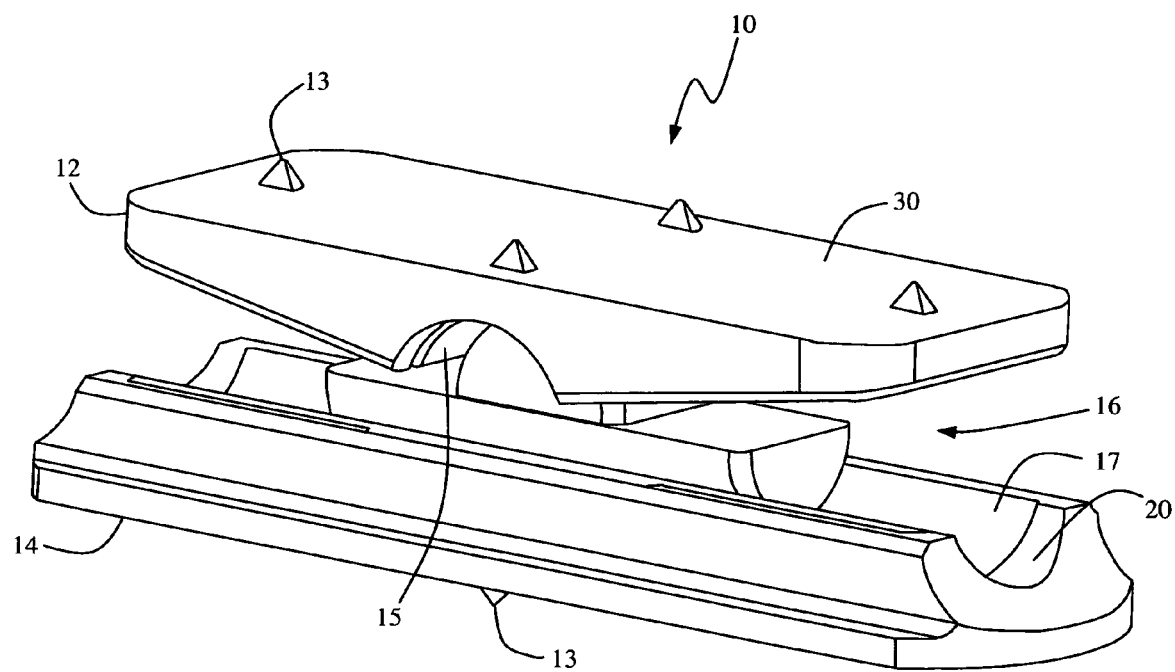
FIG. 3 is a perspective view of the total disc replacement system of FIG. 1.
Figure 4:
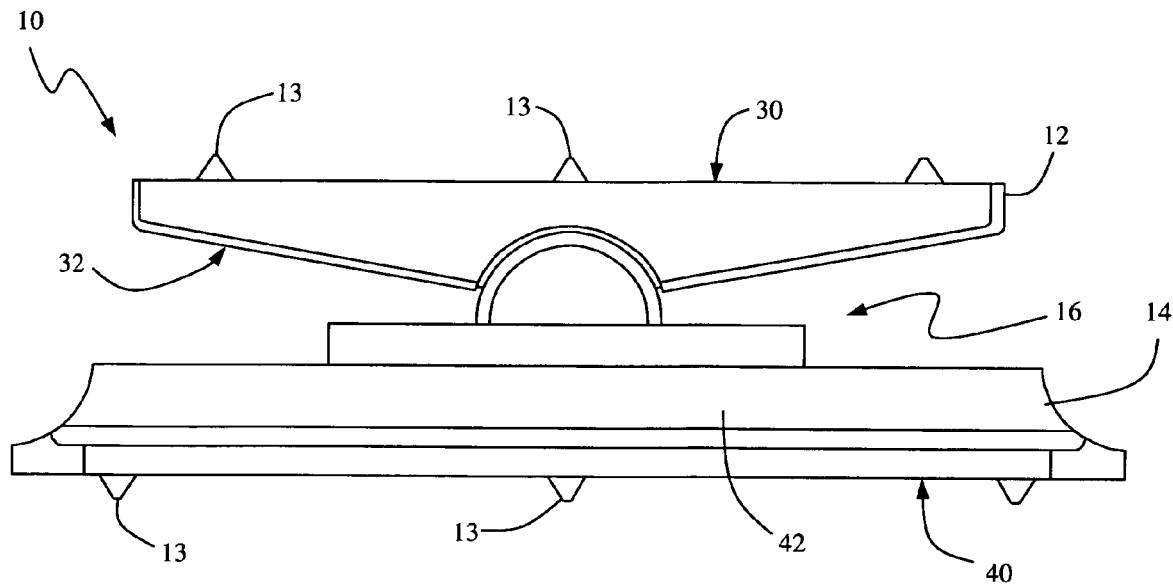
FIGS. 4-5 are side and end views, respectively, of the total disc replacement system of FIG. 1.
Figure 5:
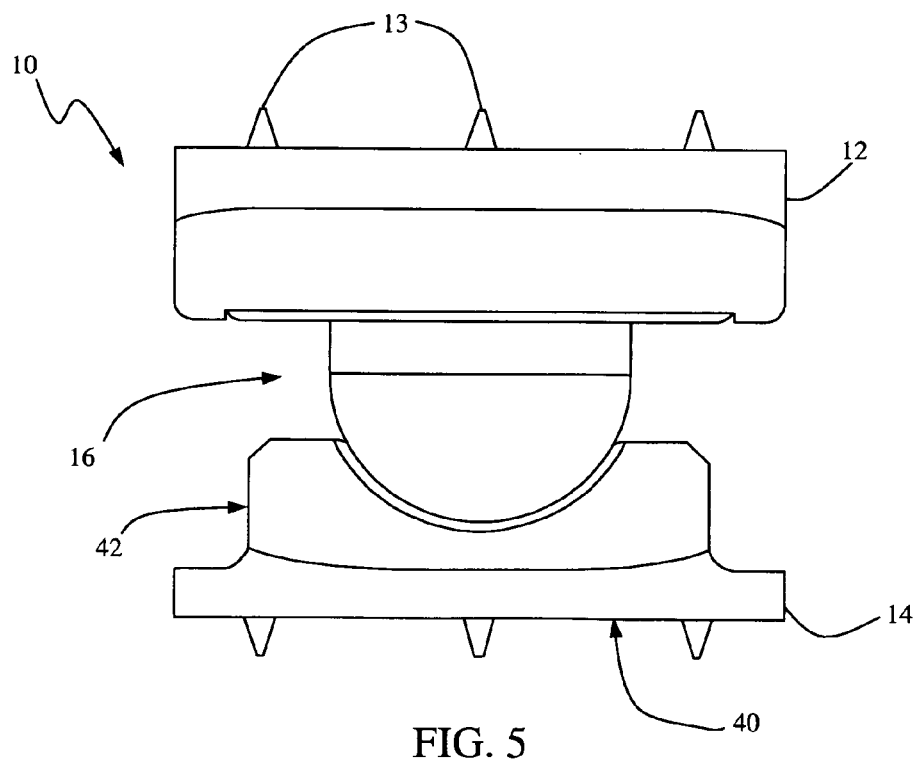
Figure 8:
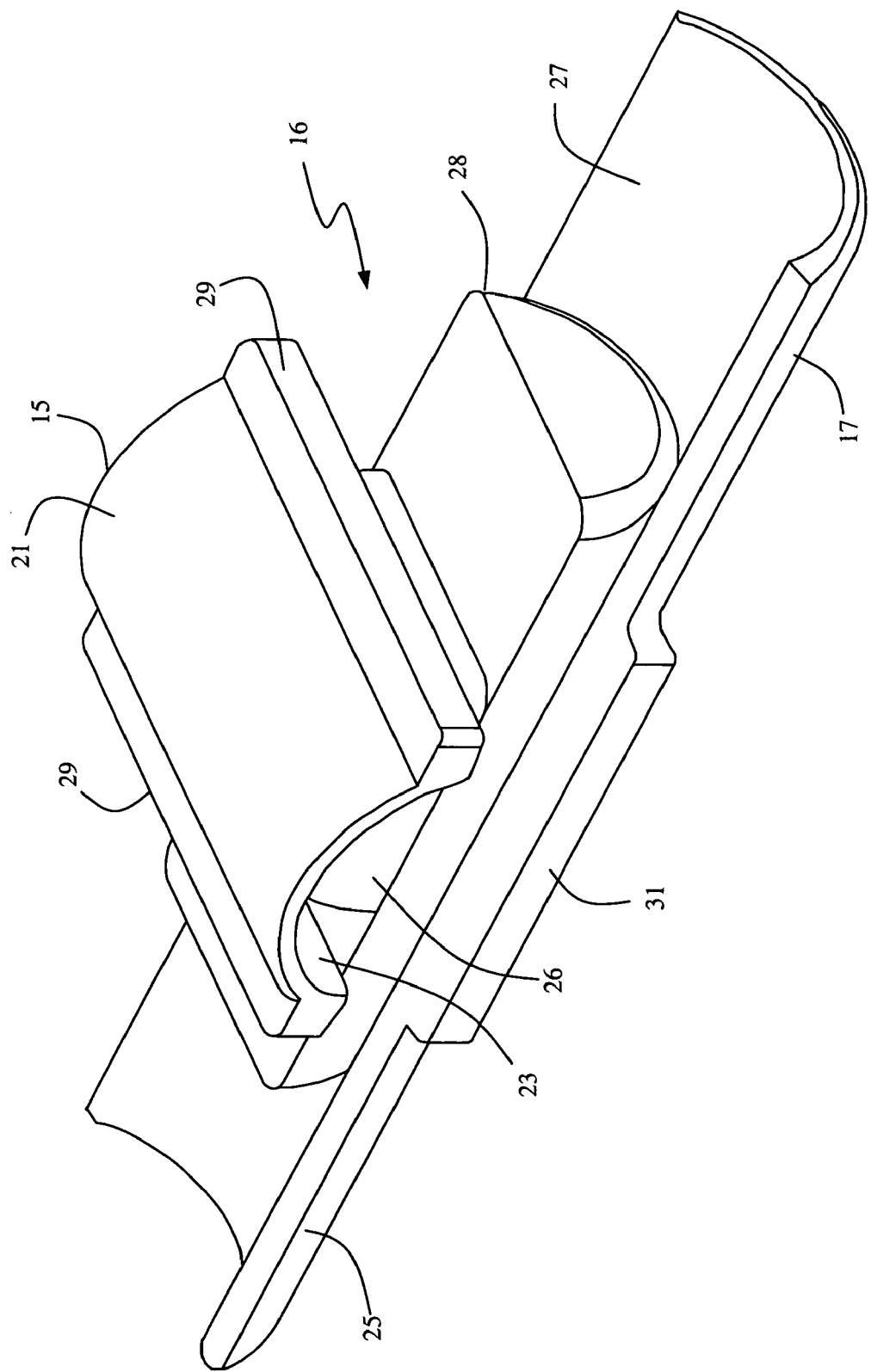
FIG. 8 is a perspective view of the intradiscal element of FIG. 6 in conjunction with a pair of intradiscal liners forming part of the total disc replacement system of FIG. 1.

Referring to FIGS. 1-2, first anchor plate 12 includes a generally planar surface 30 for engaging against a vertebra, a pair of generally angled surfaces 32 extending in a ramp-like fashion away from the semi-cylindrical surface 18 towards the lateral edges of the first anchor plate 12, and a pair of recessed regions 44. The angled surfaces 32 serve to limit the relative rotation about the Z-axis. That is, the first anchor plate 12 will be able to rotate about the Z-axis until an angled surface 32 comes into contact with another structure, such as the second intradiscal element 28 or the second anchor plate 14 (e.g., if the second intradiscal element 28 is shorter or if the intradiscal element 16 is spherical). As will be described in greater detail below, the second intradiscal element 28 may have a generally flat or angled surface against which the angled surfaces 32 may abut to accomplish the desired rotational limitation in the Z-axis. Recessed regions 44 are provided at the approximate mid-line or middle of the semi-cylindrical surface 18 and are dimensioned to receive anti-rotational wings 29 of the first intradiscal liner 15. As shown in FIG. 8 and described in further detail below, the combinations of wings 29 and recessed regions 44 function to prevent any lateral or rotational movement of intradiscal liner 15 in relation to first anchor plate 12. In this fashion, intradiscal liner 15 serves as a protective intermediary between intradiscal element 16 and first anchor plate 12.

A plurality of anti-migration features 13 may be provided on the anchor plates 12, 14 to inhibit the movement of said anchor plates after introduction into a receiving area within a vertebra. In one embodiment, the anti-migration features 13 comprise protrusions having a generally triangular cross-section, although any number of suitable configurations or anti-migration elements may be employed without departing from the scope of the present invention. Any number of mechanisms or techniques may be employed to introduce anchor plates 12, 14 into a vertebra, including but not limited to providing one or more lumens 36 (shown more clearly in FIG. 13) in the first anchor plate for coupling to or engaging with an insertion tool (not shown).

Second anchor plate 14 includes a generally planar surface 40 (FIGS. 4-5) for engaging against a vertebra, a pair of generally angled surfaces 42, and a pair of recessed regions 46. The recessed regions 46 are provided at the approximate mid-line or middle of the semi-cylindrical surface 20 and are dimensioned to receive anti-migration wings 31 of the second intradiscal liner 17. As shown in FIG. 8 and described in further detail below, the combinations of wings 31 and recessed regions 46 function to prevent any lateral or rotational movement of intradiscal liner 17 in relation to second anchor plate 14. In this fashion, intradiscal liner 17 serves as a protective intermediary between intradiscal element 16 and second anchor plate 14.

Figure 9:
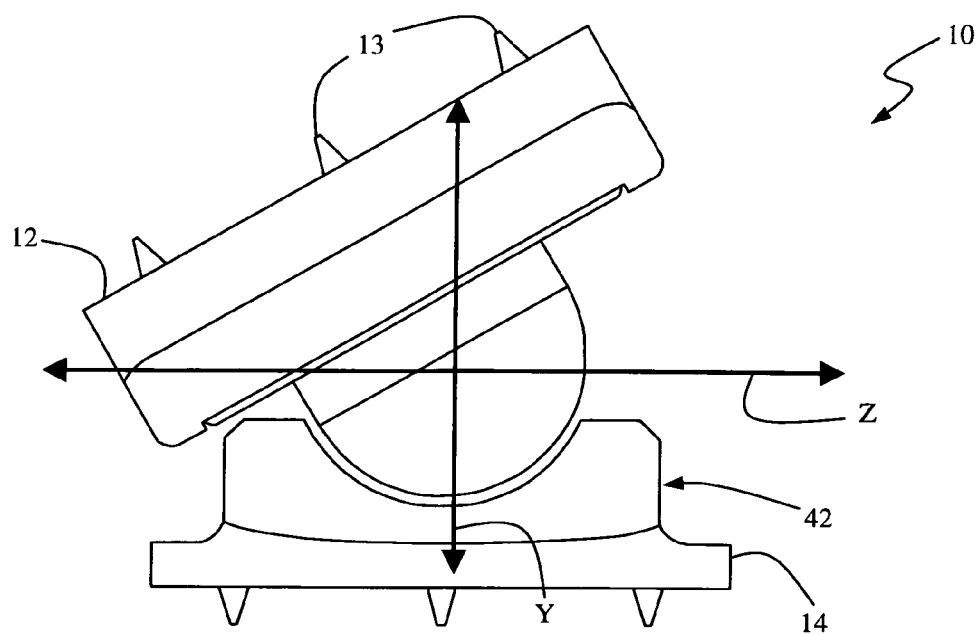
FIG. 9 is a side view of the total disc replacement system of FIG. 1, illustrating rotation about the X-axis.
Figure 10:
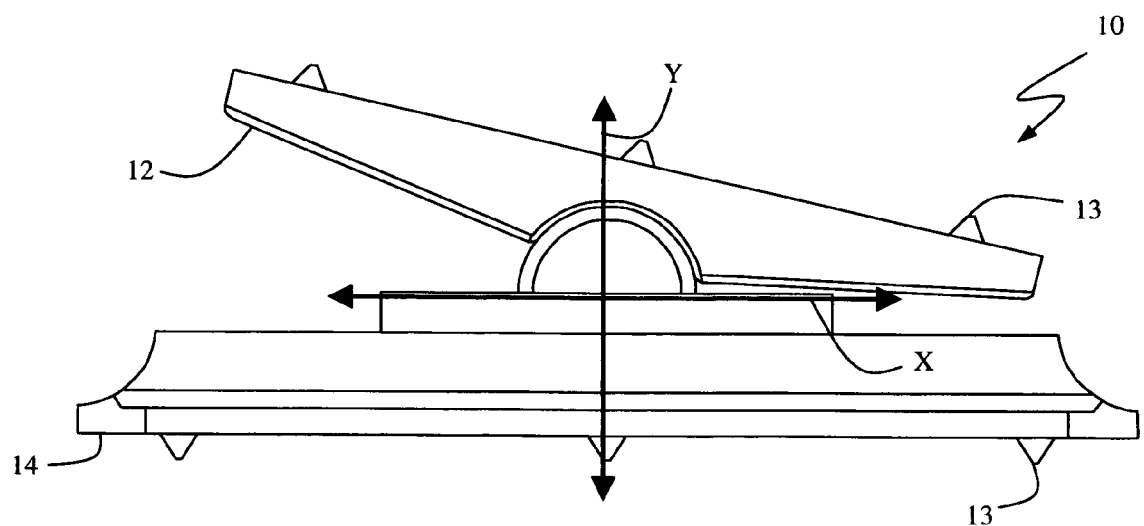
FIG. 10 is a front view of the total disc replacement system of FIG. 1, illustrating rotation about the Z-axis.
Figure 11:
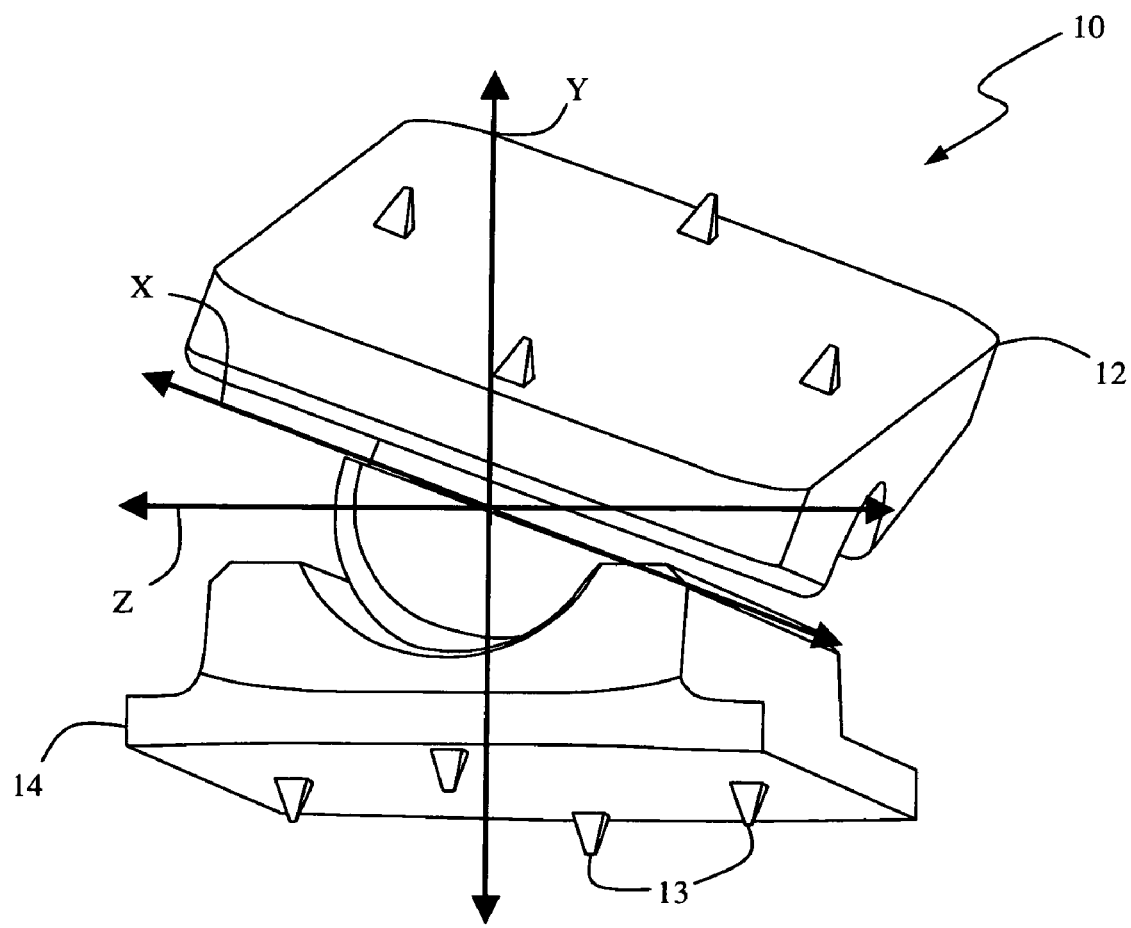
FIG. 11 is a side perspective view of the total disc replacement system of FIG. 1, illustrating extreme range of motion about the X, Y, and Z axes.

The generally angled surfaces 42 extend in a generally vertical fashion away from the semi-cylindrical surface 20 towards the anterior edge of the second anchor plate 14. The angled surface 42 serves two functions. The first function, as shown in FIG. 9, is to limit the relative rotation along the X-axis. That is, the second anchor plate 14 will be able to rotate about the X-axis until the angled surfaces 42 come into contact with the first anchor plate 12. The second function is to act in concert with the generally angled surface 32 of the first anchor plate 12 to facilitate the introduction of the intradiscal element 16. That is, if the first and second anchor plates 12, 14 are introduced first, then the angled surfaces 32, 42 will serve as a ramp over which the intradiscal element 16 may pass in order to become seated in an articulating relationship with surfaces 23, 27 of the first and second intradiscal liners 15, 17 (described in greater detail below). In this fashion, the ramp effect of the angled surfaces 32, 42 will cause the first and second anchor plates 12, 14 (and their respective vertebrae) to gently distract to receive the intradiscal element 16.

The second anchor plate 14 may be equipped with the same anti-migration features 13 discussed above with reference to anchor plate 12 such that a repeat discussion is not necessary. In similar fashion described above with reference to the first anchor plate 12, any number of mechanisms or techniques may be employed to introduce the second anchor plate 14 into a vertebra, including but not limited to providing one or more lumens 36 in the first anchor plate for coupling to or engaging with an insertion tool (not shown).

The first and second anchor plates 12, 14 each have a generally rectangular shape including a width of less than 25 mm. Dimensioning the first and second anchor plates 12, 14 in this fashion advantageously provides the ability to advance the TDR system 10 through a minimal access surgical corridor. It also advantageously provides the ability to introduce the TDR system 10 into the spine using a generally lateral approach. Depending upon the particular patient, and the location within the particular vertebral level within that patient, the anchor plates 12, 14 may be provided with a length in the range of between 15 mm and 40 mm.

The first and second anchor plates 12, 14 may be constructed from any number of materials and/or compositions suitable for medical applications, including but not limited to metallic compositions or alloys (such as Co—Cr—Mo), ceramics (such as zirconia and/or alumina), polymers (such as ultra-high molecular weight polyethylene), and/or any combination thereof. Where beneficial and appropriate, either or both of the first and second anchor plates 12, 14 may also be coated with any number of suitable compositions, such as zirconium oxide coating found in U.S. Pat. No. 5,037,438, the contents of which are hereby incorporated into this disclosure as if set forth in its entirety.

FIGS. 6-7 illustrate the intradiscal element 16 in greater detail. In this embodiment, the intradiscal element 16 includes the first intradiscal element 26 rotatably coupled to the second intradiscal element 28. By way of example only, this rotational relationship is accomplished by providing a post element 48, an aperture 52, and a snap-ring 56. The post element 48 extends from a generally planar surface 50 of the first intradiscal element 26, and preferably from the approximate center thereof. The post element 48 includes a groove dimensioned to receive the snap-ring 56 in a biased configuration therein. The aperture 52 is formed in a generally planar surface 54 of the second intradiscal element 28 (preferably in the approximate center thereof), and the optional snap-ring 56 is dimensioned to be engaged within a groove formed along the post element 48 and a groove 60 formed within the aperture 52.

FIG. 6 best illustrates the aspect of rotation between the first and second intradiscal elements 26, 28. The first and second intradiscal elements 26, 28 may be initially oriented in any number of different manners, including but not limited to the generally perpendicular orientation shown. From this position, the first and second intradiscal elements 26, 28 may be rotated about the Y-axis in the range ∂3 of between 0 and 20 degrees in either direction from the Z-axis (within the plane of the generally planar surfaces 50, 54 of the first and second intradiscal elements 26, 28). If the TDR system 10 is provided for placement via a lateral approach (shown by way of example), this would allow the first anchor plate 12 to rotate relative to the second anchor plate 14 in the range of between 0 and 20 degrees in either direction about the Y-axis.

In addition to the rotational capability about the Y-axis, the first articular surface 22 is dimensioned to articulate with the second surface 23 of the first intradiscal liner 15, while the second articular surface 24 is dimensioned to articulate with the second surface 27 of the second intradiscal liner 17. Since the first intradiscal liner 15 is embedded in the semi-cylindrical surface 18 of the first anchor plate 12, and the second intradiscal liner 17 is embedded in the semi-cylindrical surface 20 of the second anchor plate 14, this enables the first anchor plate 12 to rotate relative to the intradiscal element 16 about the Z-axis, and the second anchor plate 14 to rotate relative to the intradiscal element 16 about the X-axis. As noted above, this also enables the first anchor plate 12 to translate relative to the intradiscal element 16 in either direction along the Z-axis, and the second anchor plate 14 to translate relative to the intradiscal element 16 in either direction along the X-axis. In this fashion, the TDR system 10 of this first embodiment provides rotation along three distinct axes (X, Y, Z) and translation along two distinct axes (X and Z).

In some situations, it may be advantageous for intradiscal element 16 to be provided as a unitary member. FIG. 6A illustrates one example of an intradiscal element 16a provided as a unitary member, in which intradiscal element 16a includes a first portion 22a having a first articular surface 26a and a second portion 24a having a second articular surface 28a. First articular surface 26a and second articular surface 28a may each be provided with a generally arcuate cross-section. The first articular surface 26a is dimensioned to articulate with the second surface 23 of the first intradiscal liner 15 such that, by extension, the first anchor plate 12 may rotate relative to the intradiscal element 16a about the Z-axis (FIGS. 6A & 10), as well as translate relative to the intradiscal element 16a in either direction along the Z-axis (denoted as line "$T_Z$"). The second articular surface 28a is dimensioned to articulate with the second surface 27 of the second intradiscal liner 17 such that, by extension, the second anchor plate 14 may rotate relative to the intradiscal element 16a about the X-axis (FIGS. 6A & 9), as well as translate relative to the intradiscal element 16a in either direction along the X-axis (denoted as line "$T_X$"). In this fashion, rotation about the Z-axis will always occur at the same location along the first anchor plate 12 and rotation about the X-axis will always occur at the same location along the second anchor plate 14.

The intradiscal element 16 of the present invention may be constructed from any number of materials and/or compositions suitable for medical applications, including but not limited to metallic compositions or alloys (such as Co—Cr—Mo), ceramics (such as zirconia and/or alumina), polymers (such as ultra-high molecular weight polyethylene), and/or any combination thereof. Where beneficial and appropriate, the intradiscal element 16 may also be coated with any number of suitable compositions, such as zirconium oxide coating found in U.S. Pat. No. 5,037,438, the contents of which are hereby incorporated into this disclosure as if set forth in its entirety.

FIG. 8 illustrates intradiscal liners 15, 17 in greater detail. The first intradiscal liner 15 includes a first surface 21, a second surface 23, each having a generally arcuate cross-section, and a pair of anti-migration wings 29. The first surface 21 is dimensioned to fit into the semi-cylindrical surface 18 of the first anchor plate 12. Accordingly, the length of the first intradiscal liner 15 traverses the width of the first anchor plate 12. As such, the length of the first intradiscal liner 15 may not exceed, and is generally slightly less than, the width of the first anchor plate 12. The second surface 23 is dimensioned to interact with the first articular surface 22 of intradiscal element 16. As such, this allows the first intradiscal liner 15 to form a barrier between the intradiscal element 16 and the first anchor plate 12. This barrier serves to reduce friction between the first anchor plate 12 and intradiscal element 16, ultimately enhancing the durability of the total disc replacement system 10. Anti-migration wings 29 serve to prevent the first intradiscal liner 15 from rotating and/or translating with respect to first anchor plate 12.

The second intradiscal liner 17 includes a first surface 25, a second surface 27, each having a generally arcuate cross-section, and a pair of anti-migration wings 31. The first surface 25 is dimensioned to fit into the semi-cylindrical surface 20 of the second anchor plate 14. Accordingly, the length of the second intradiscal liner 17 traverses the length of the second anchor plate 14. As such, the length of the second intradiscal liner 17 may not exceed, and is generally slightly less than, the length of the second anchor plate 14. The second surface 27 is dimensioned to interact with the second articular surface 24 of intradiscal element 16. As such, this allows the second intradiscal liner 17 to form a barrier between the intradiscal element 16 and the second anchor plate 14. This barrier serves to reduce friction between the second anchor plate 14 and intradiscal element 16, ultimately enhancing the durability of the total disc replacement system 10. Anti-migration wings 31 serve to prevent the second intradiscal liner 17 from rotating and/or translating with respect to second anchor plate 14.

The intradiscal liners 15, 17 of the present invention may be constructed from any number of materials and/or compositions suitable for medical applications, including but not limited to metallic compositions or alloys (such as Co—Cr—Mo), ceramics (such as zirconia and/or alumina), polymers (such as ultra-high molecular weight polyethylene), and/or any combination thereof. Where beneficial and appropriate, the intradiscal liners 15, 17 may also be coated with any number of suitable compositions, such as zirconium oxide coating found in U.S. Pat. No. 5,037,438, mentioned above. The intradiscal liners 15, 17 may be secured to the semi-cylindrical surfaces 18, 20 of the first and second anchor plates 12, 14 by any suitable method or material, including but not limited to biocompatible adhesive substances, brazing, and the like.

Figure 12:
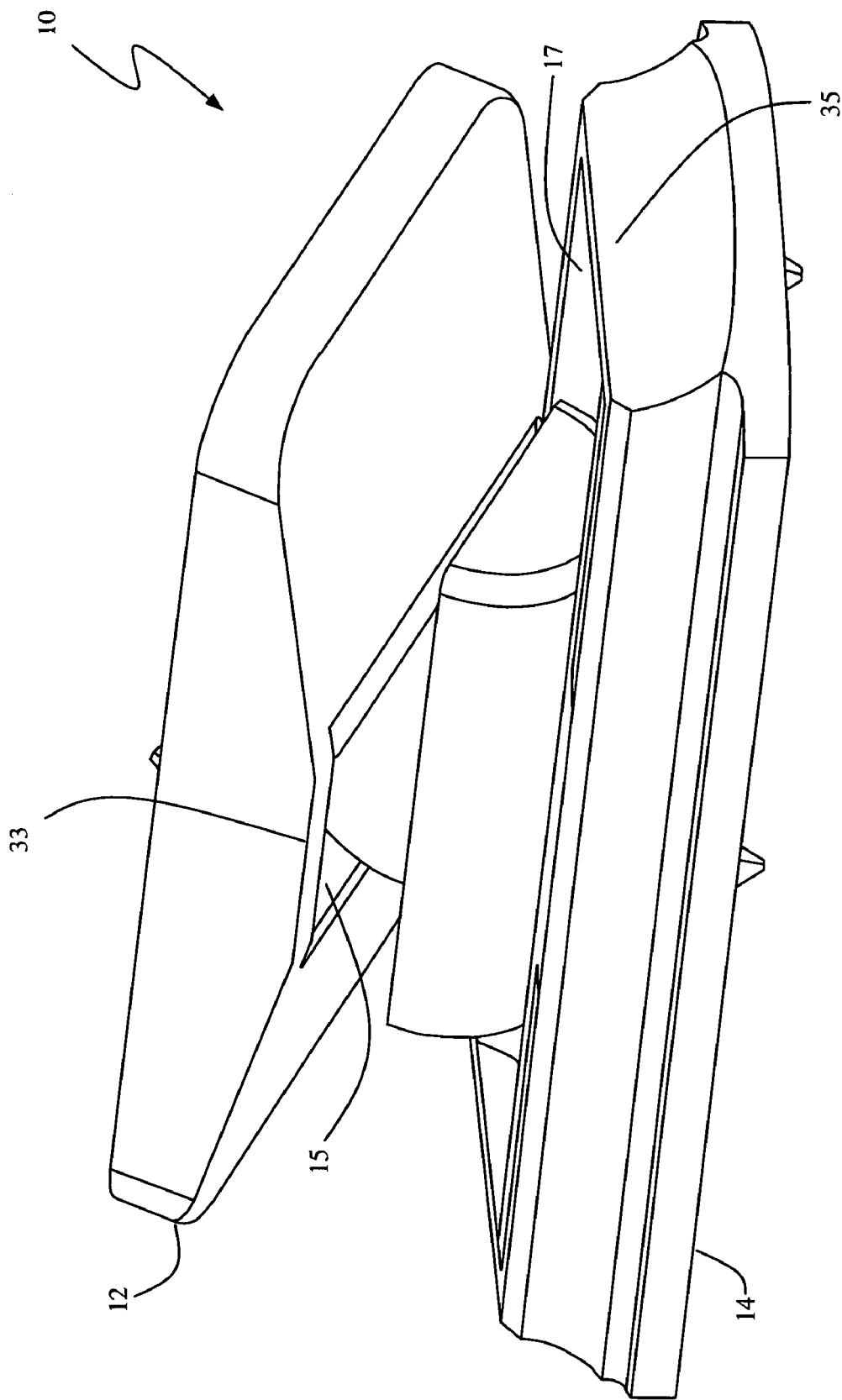
FIG. 12 is a perspective view of the total disc replacement system according to one embodiment of the present invention, illustrating the use of endplates to further constrain lateral movement of the intradiscal element.

FIG. 12 illustrates an alternative embodiment of the TDR system 10 of the present invention, wherein the first and second anchor plates 12, 14 contain a first and second pair of endcaps 33, 35, respectively. Endcaps 33, 35 function to prevent the intradiscal liners 15, 17 from moving in a laterally along the semi-cylindrical surfaces 18, 20 of the first and second anchor plates 12, 14.

Figure 13:
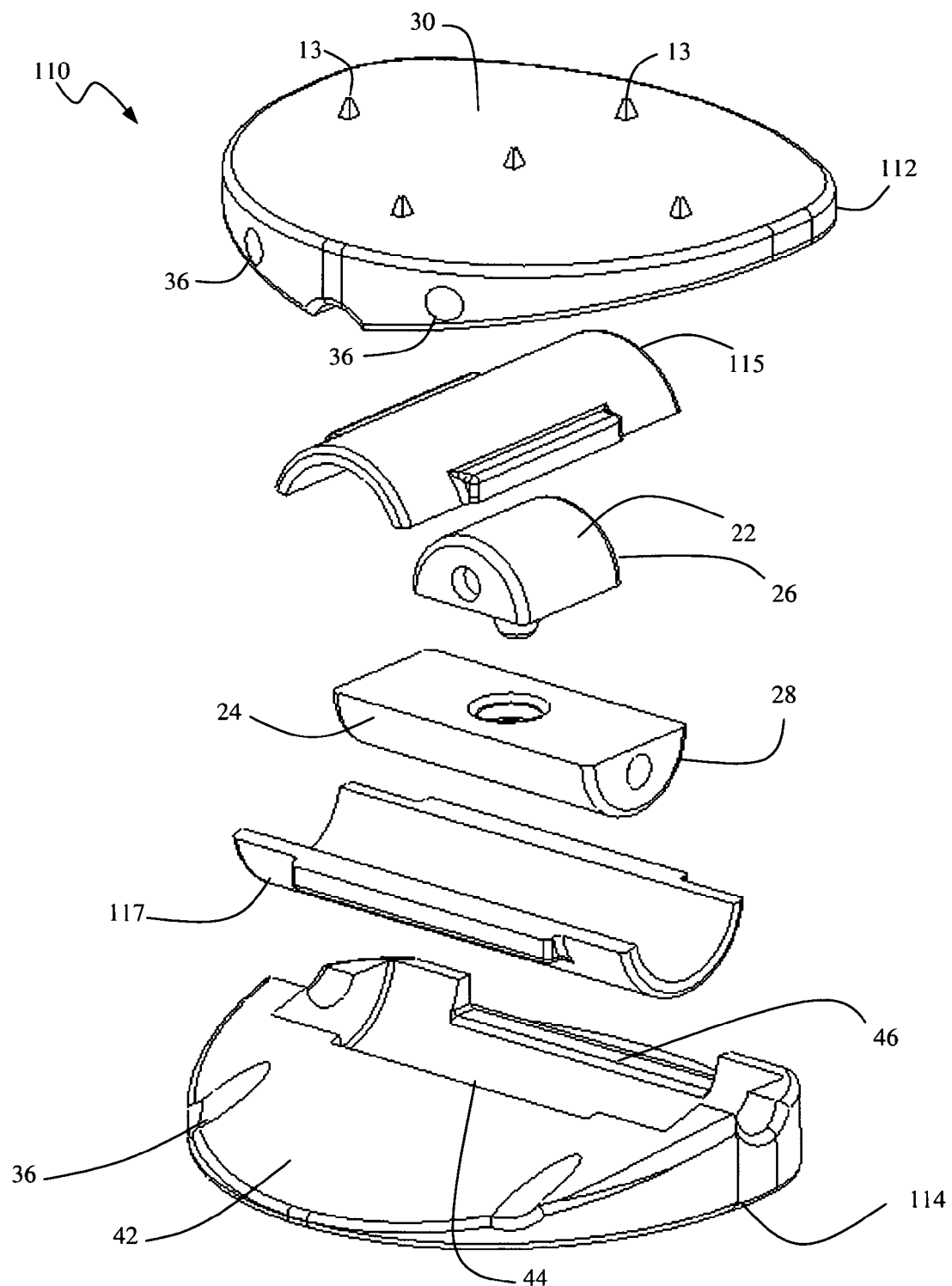
FIG. 13 is an exploded perspective view of a total disc replacement system according to a second embodiment of the present invention.

FIG. 13 illustrates a total disc replacement (TDR) system 110 according to a second embodiment of the present invention. The TDR system 110 is designed to operate in the same fashion as the TDR system 10 shown and described above, except that the TDR system 110 is particularly suited for anterior access introduction into the spine. (For the sake of clarity, all features or components in common with the TDR system 10 will be numbered identically to those features, all features similar in function but different in form will be numbered +100, and reference can be made to the discussion above regarding the TDR system 10, rendering a repeat discussion unnecessary and optional). The central distinction between TDR system 10 and TDR system 110 is that the first and second anchor plates 112, 114 each have a generally cylindrical shape. Dimensioning the first and second anchor plates 112, 114 in this fashion is advantageous when a minimal access surgical corridor is not required. Related to the generally cylindrical shape of the first anchor plate 112 is an increased length of first intradiscal liner 115 compared to first intradiscal liner 15. First intradiscal liner 115 is still dimensioned to be slightly less than the length of the first anchor element 112.

FIGS. 14-18 illustrate a total disc replacement (TDR) system 210 according to a third embodiment of the present invention. The TDR system 210 includes a first anchor plate 212, a second anchor plate 214, a first pair of intradiscal liners 216, a second pair of intradiscal liners 218, and an intradiscal element 220. Each anchor plate 212, 214 is equipped with a plurality of anchor elements 222 and a cutout region 224, 226, respectively. The first pair of intradiscal liners 216 each have a first surface 228 dimensioned to fit into the cut-out region 224 of the first anchor plate 212, a second generally planar surface 230, and a semi-cylindrical articular surface 232 dimensioned to articulate with the intradiscal element 220. The second pair of intradiscal liners 218 each have a first surface 234 dimensioned to fit into the cut-out region 226 of the second anchor plate 214, a second generally planar surface 236, and a semi-cylindrical articular surface 238 dimensioned to articulate with the intradiscal element 220.

Figure 23:
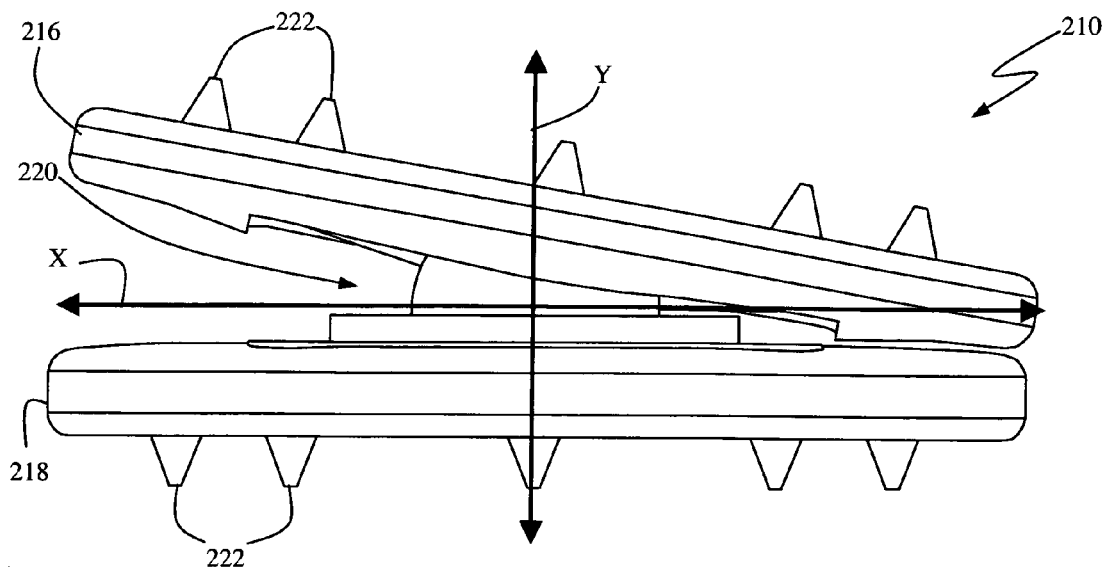
FIG. 23 is a front view of the total disc replacement system of FIG. 16, illustrating rotation about the Z-axis.
Figure 24:
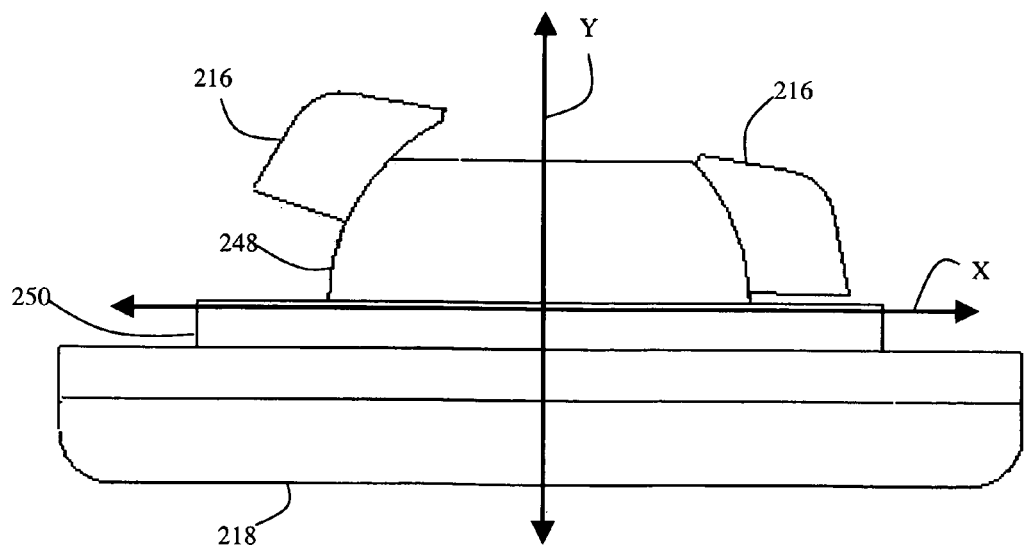
FIG. 24 is a front view of the total disc replacement system of FIG. 23 with the first and second anchor plates removed, illustrating the position of the intradiscal liners upon rotation about the Z-axis.

The intradiscal element 220 includes a first and second pair of articular surfaces 240, 242 each having a generally arcuate cross-section, and a pair of generally planar surfaces 244, 246. The first pair of articular surfaces 240 are dimensioned to articulate with the semi-cylindrical articular surfaces 232 of the first pair of intradiscal liners 216 such that, by extension, the first anchor plate 212 may rotate relative to the intradiscal element 220 about the Z-axis (FIGS. 19, 23, 24), as well as translate relative to the intradiscal element 220 in either direction along the Z-axis (denoted as line "$T_Z$"). The second pair of articular surfaces 242 are dimensioned to articulate with the semi-cylindrical articular surfaces 238 of the second pair of intradiscal liners 218 such that, by extension, the second anchor plate 214 may rotate relative to the intradiscal element 220 about the X-axis (FIGS. 19, 25, 26), as well as translate relative to the intradiscal element 220 in either direction along the X-axis (denoted as line "$T_X$"). In this fashion, rotation about the Z-axis will always occur at the same location along the first anchor plate 212 and rotation about the X-axis will always occur at the same location along the second anchor plate 214. The generally planar surfaces 244, 246 may be located opposite one another and function to reduce the overall profile of the TDR system 210 of the present invention. The intradiscal element 220 may optionally (by way of example only) comprise a first intradiscal pivot 248 rotatably coupled to a second intradiscal pivot 250, which allows relative rotation about the Y-axis. In use, then, the TDR system 210 of this first embodiment provides rotation along three distinct axes (X, Y, Z) and translation along two distinct axes (X and Z).

When used within the lumbar spine, for example, it may be desirable to configure the second anchor plate 214 such that the cutout region 226 (and hence X-axis) is located within the posterior one-third of the disc space (and generally within the frontal plane of the patient) to approximate the axis of rotation of the natural spine during flexion and extension. It may similarly be desirable to configure the first anchor plate 212 such that the cutout region 224 (and hence Z-axis) is located at the approximate center of the disc space (and generally within the sagittal plane of the patient) to approximate the axis of rotation of the natural spine during lateral bending. Although described by way of example in this configuration, it will be appreciated that the relative position of the cutout regions 224, 226 may be altered in any number of different fashions depending upon the vertebral level (i.e. cervical, thoracic, and/or lumbar) as well as the directional approach employed to place the TDR system 210 into a disc space (e.g., lateral, anterior, postero-lateral, antero-lateral). Moreover, it will be appreciated that the TDR system 210 may be introduced into a disc space in the orientation shown (with the first anchor plate 212 "above" the second anchor plate 214 such that the anchor elements 222 are to be disposed within a respective "upper" and "lower" vertebral level within the patient) or vice versa.

Figure 14:
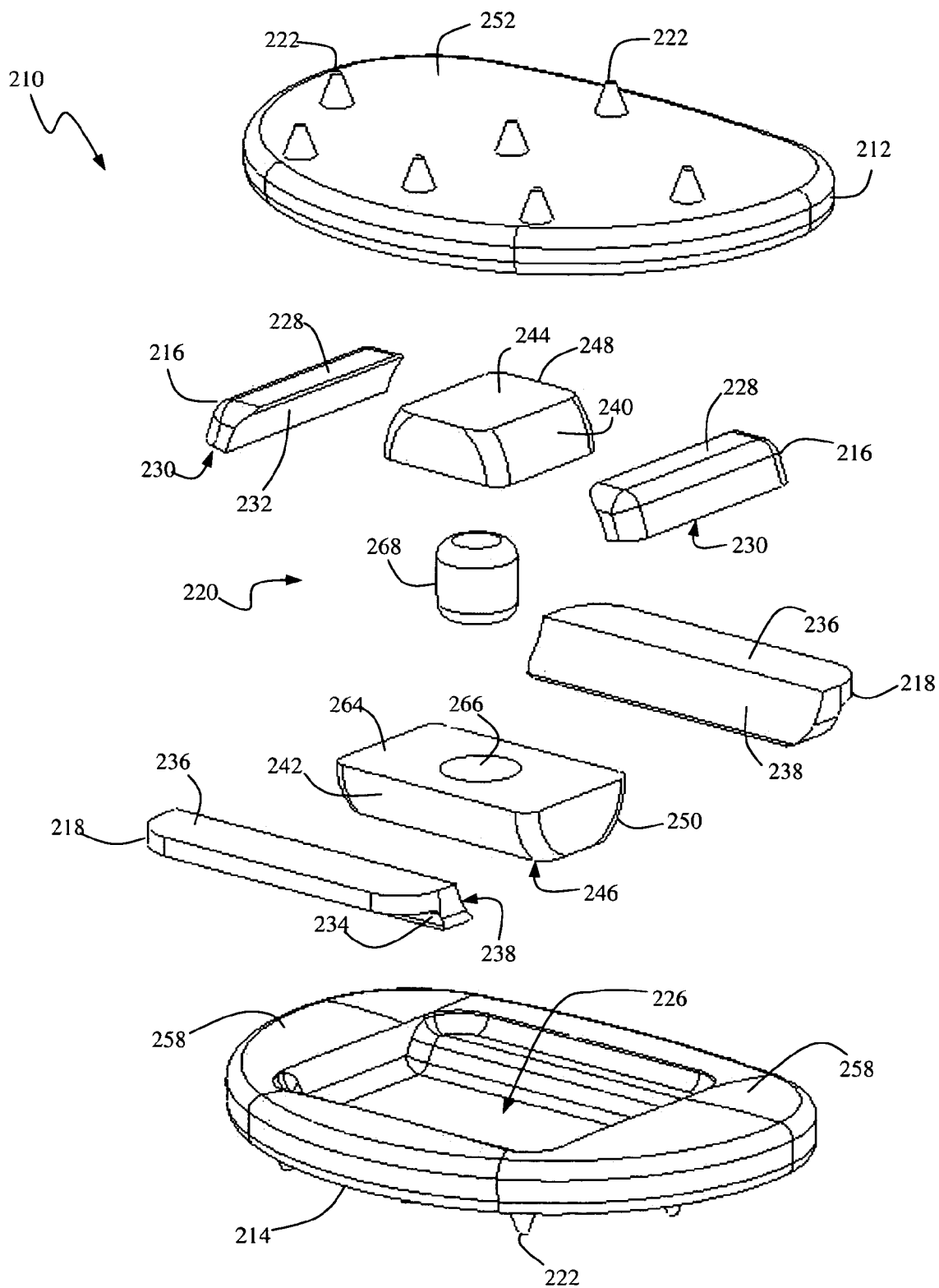
FIG. 14 is an exploded perspective view of a total disc replacement system according to a third embodiment of the present invention.
Figure 15:
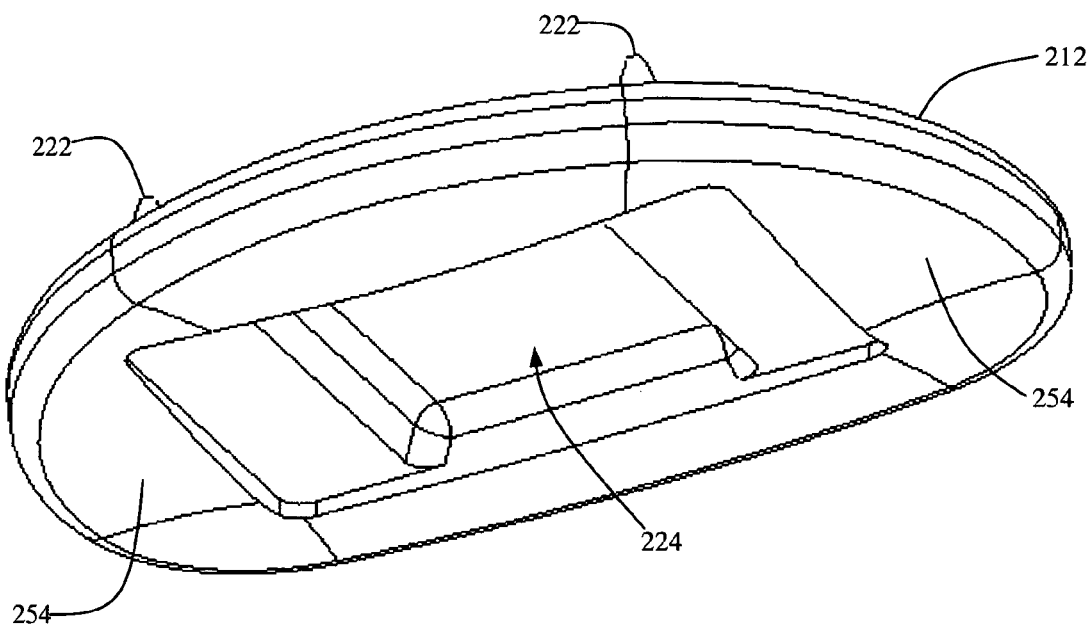
FIG. 15 is a perspective view of the underside of a first anchor plate forming part of the total disc replacement system of FIG. 14.
Figure 16:
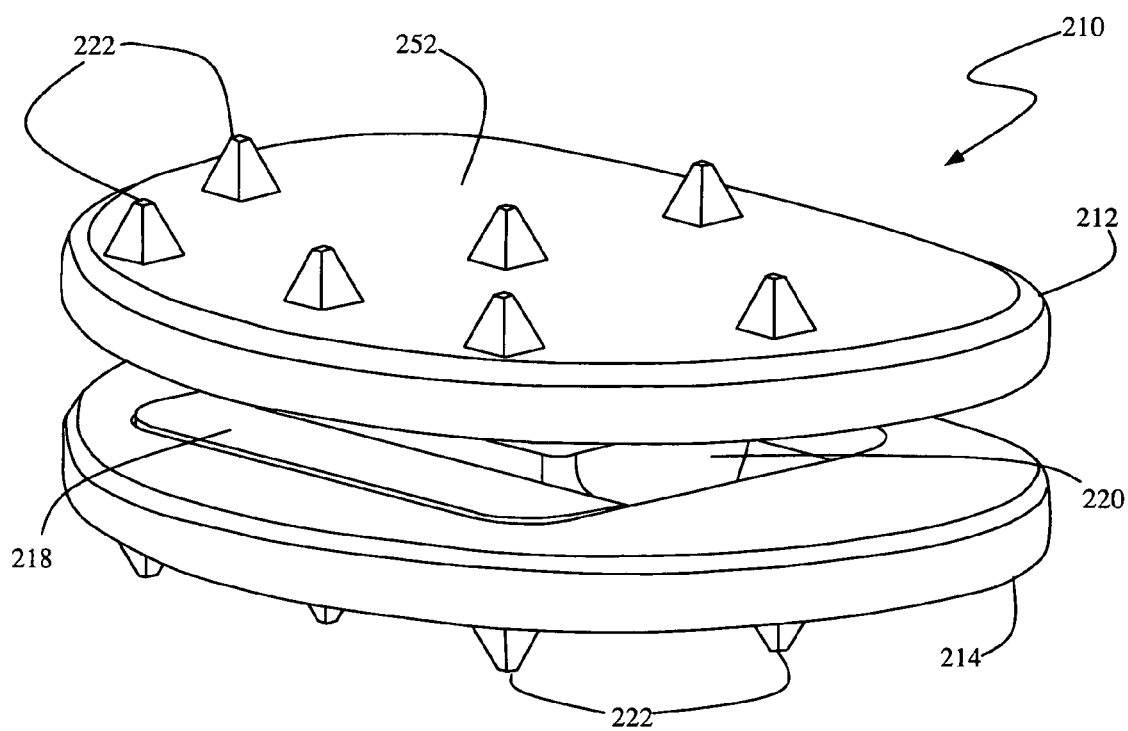
FIG. 16 is a perspective view of the fully assembled total disc replacement system of FIG. 14.
Figure 17:
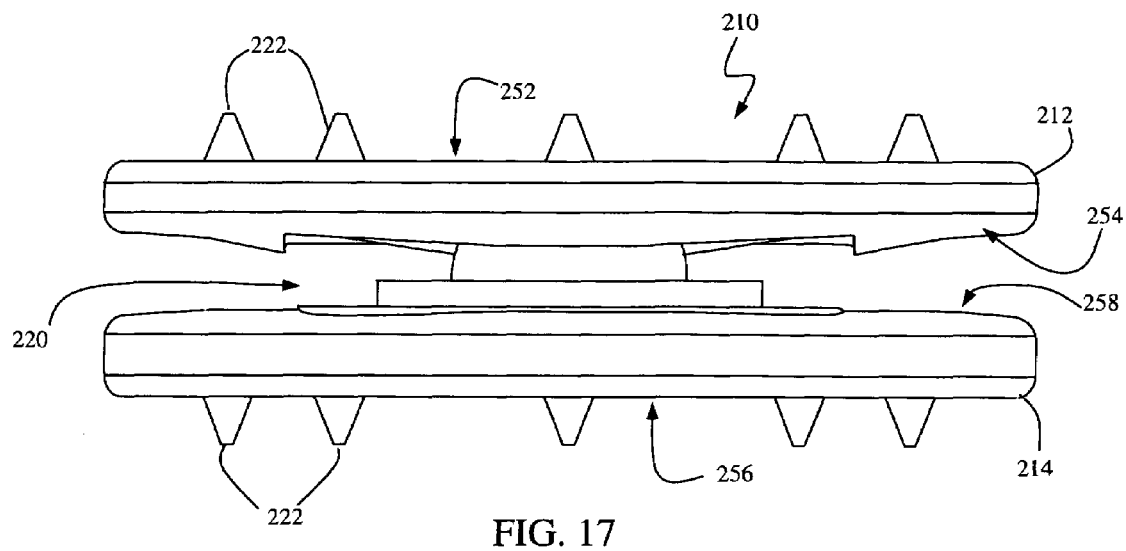
FIGS. 17-18 are front and side views, respectively, of the total disc replacement system of FIG. 14.
Figure 18:
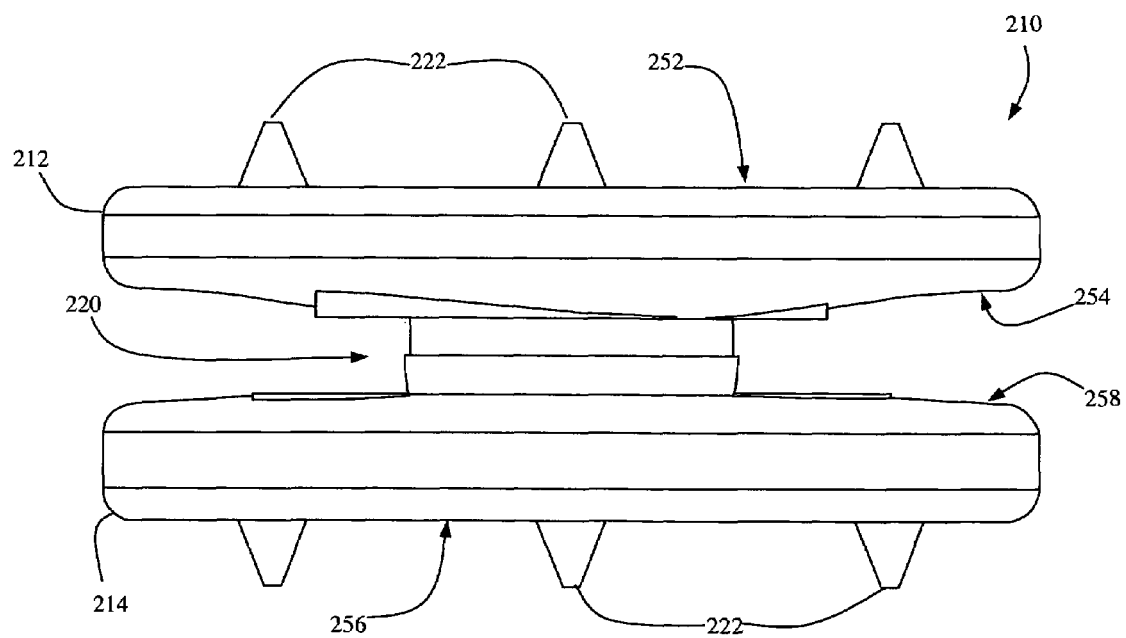

Referring to FIGS. 14-15, the first anchor plate 212 includes a generally planar surface 252 for engaging a vertebra and a pair of generally angled surfaces 254, which may extend in a ramp-like fashion away from the cutout region 224 towards the lateral edges of the first anchor plate 212. The generally angled surfaces 254 serve to limit the relative rotation of the TDR system 210 about the Z-axis. That is, the first anchor plate 212 will be able to rotate about the Z-axis until a generally angled surface 254 comes into contact with another structure, such as the second intradiscal pivot 250 or the second anchor plate 214 (e.g., if the second intradiscal pivot 250 is shorter or if the intradiscal element 220 is spherical). As will be described in greater detail below, the second intradiscal pivot 250 may have a generally planar surface 264 against which the generally angled surfaces 254 may abut to accomplish the desired rotational limitation in the Z-axis. A cutout region 224 may be provided at the approximate mid-line or middle of the first anchor plate 212 and is dimensioned to receive a first pair of intradiscal liners 216. The cutout region 224 functions to prevent any lateral or rotational movement of the first pair of intradiscal liners 216 in relation to first anchor plate 212, as well as to reduce the overall profile of the TDR system 210 of the present invention. In this fashion, the first pair of intradiscal liners 216 serves as a protective intermediary between intradiscal element 220 and first anchor plate 212.

A plurality of anti-migration features 222 may be provided on the anchor plates 212, 214 to inhibit the movement of said anchor plates after introduction into a receiving area within a vertebra. In one embodiment, the anti-migration features 222 may comprise protrusions having a generally triangular cross-section, although any number of suitable configurations or anti-migration elements may be employed without departing from the scope of the present invention. Any number of mechanisms or techniques may be employed to introduce anchor plates 212, 214 into a vertebra, including but not limited to providing one or more lumens and/or grooves (not shown) in the first anchor plate for coupling to or engaging with an insertion tool (not shown).

Second anchor plate 214 includes a generally planar surface 256 (FIGS. 17-18) for engaging a vertebra, a pair of generally angled surfaces 258, and a cutout region 226. Cutout region 226 may be provided at the approximate mid-line or middle of the second anchor plate 214 and is dimensioned to receive a second pair of intradiscal liners 218. The cutout region 226 functions to prevent any lateral or rotational movement of the second pair of intradiscal liners 218 in relation to second anchor plate 214, as well as reduce the overall profile of the TDR system 210 of the present invention. In this fashion, the second pair of intradiscal liners 218 serves as a protective intermediary between intradiscal element 220 and second anchor plate 214.

Figure 25:
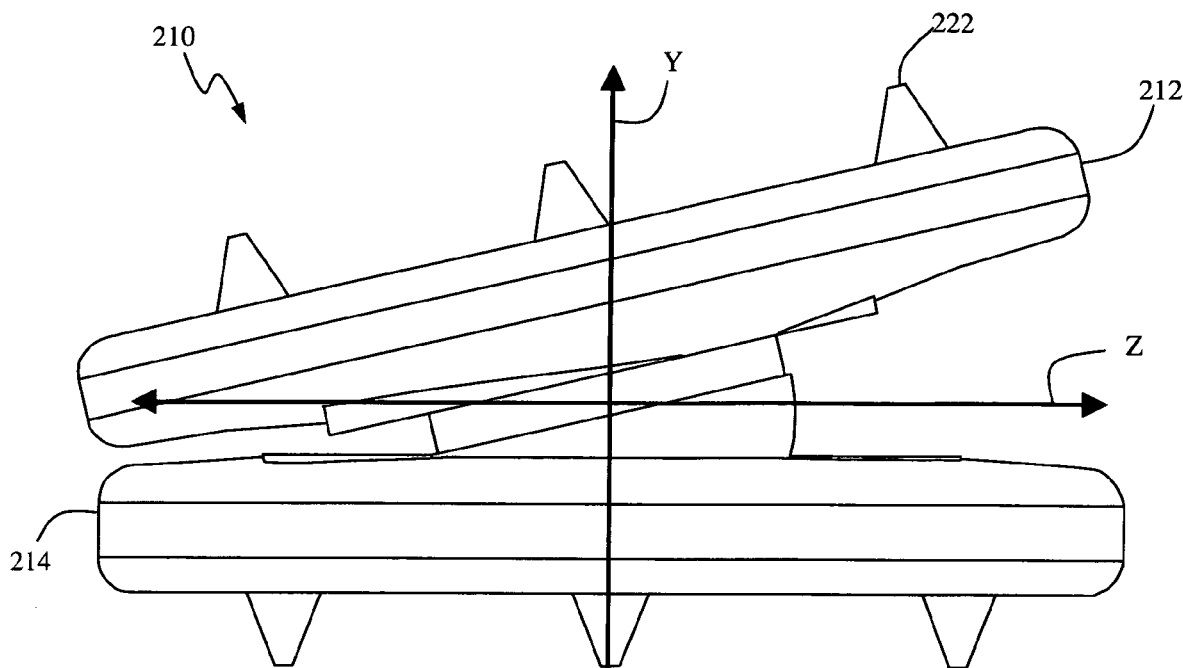
FIG. 25 is a side view of the total disc replacement system of FIG. 16, illustrating rotation about the X-axis.
Figure 26:
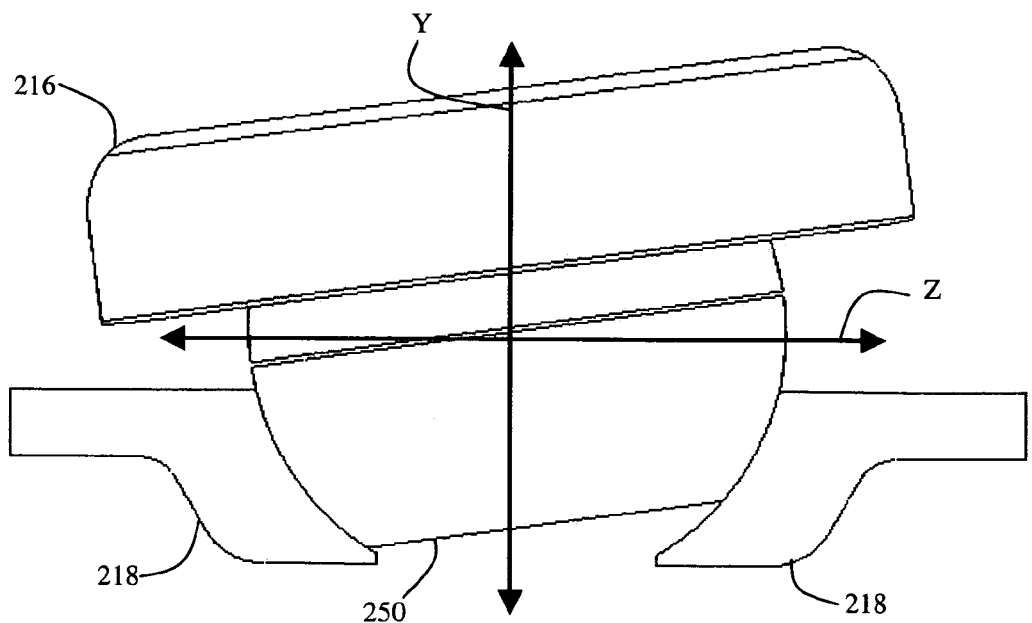
FIG. 26 is a side view of the total disc replacement system of FIG. 25 with the first and second anchor plates removed, illustrating the position of the intradiscal liners upon rotation about the X-axis.

The generally angled surfaces 258 extend in a generally lateral fashion away from the cutout region 226 towards the edges of the second anchor plate 214. The generally angled surfaces 258 serve two functions. The first function, as shown in FIG. 25, is to limit the relative rotation along the X-axis. That is, the first anchor plate 212 will be able to rotate about the X-axis until the generally angled surfaces 254 come into contact with the generally angled surfaces 258 on the second anchor plate 214. The second function is to act in concert with the generally angled surfaces 254 of the first anchor plate 212 to facilitate the introduction of the intradiscal element 220. That is, if the first and second anchor plates 212, 214 are introduced first, then the angled surfaces 254, 258 may serve as a ramp over which the intradiscal element 220 may pass in order to become seated in an articulating relationship with surfaces 232, 238 of the first and second pairs of intradiscal liners 216, 218 (described in greater detail below). In this fashion, the ramp effect of the angled surfaces 254, 258 will cause the first and second anchor plates 212, 214 (and their respective vertebrae) to gently distract to receive the intradiscal element 220.

The second anchor plate 214 may be equipped with the same anti-migration features 222 discussed above with reference to first anchor plate 212 such that a repeat discussion is not necessary. Similarly, any number of mechanisms or techniques may be employed to introduce the second anchor plate 214 into a vertebra, including but not limited to providing one or more lumens and/or grooves in the first anchor plate for coupling to or engaging with an insertion tool (not shown).

The first and second anchor plates 212, 214 may be constructed from any number of materials and/or compositions suitable for medical applications, including but not limited to metallic compositions or alloys (such as Co—Cr—Mo), ceramics (such as zirconia and/or alumina), polymers (such as ultra-high molecular weight polyethylene), and/or any combination thereof. Where beneficial and appropriate, either or both of the first and second anchor plates 212, 214 may also be coated with any number of suitable compositions, such as zirconium oxide coating found in U.S. Pat. No. 5,037,438, the contents of which are hereby incorporated into this disclosure as if set forth in its entirety.

Figure 19:
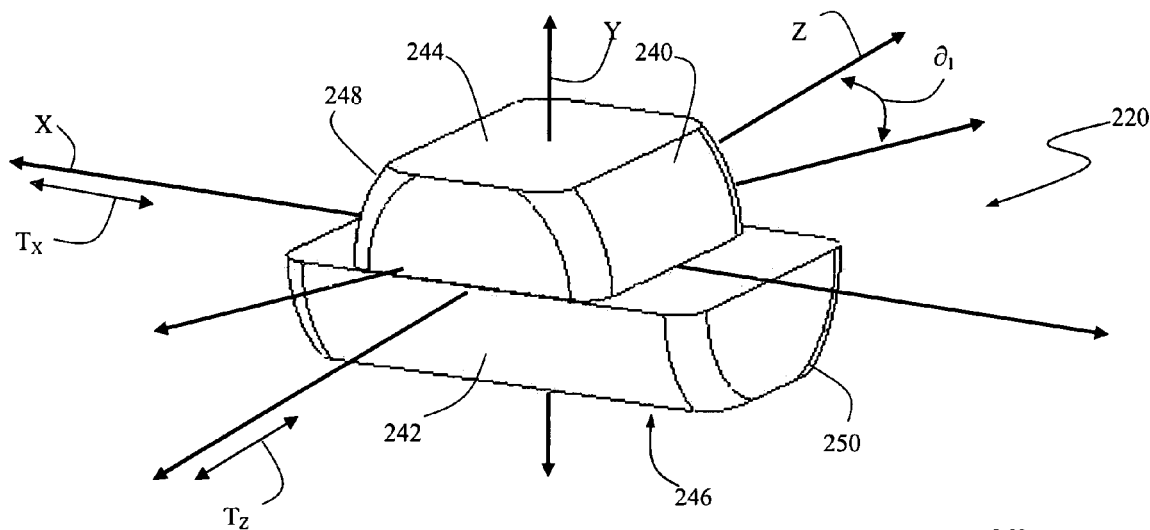
FIG. 19 is a perspective view of an intradiscal element forming part of the total disc replacement system of FIG. 14.
Figure 19A:
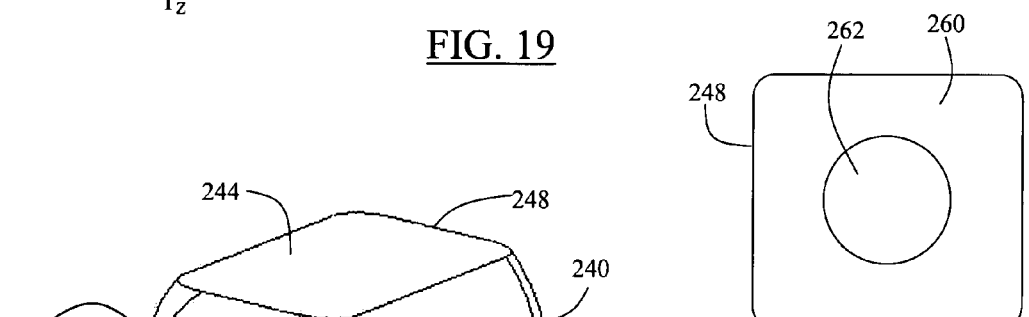
FIG. 19A is a bottom plan view of a first intradiscal pivot forming part of the intradiscal element of FIG. 19.
Figure 20:
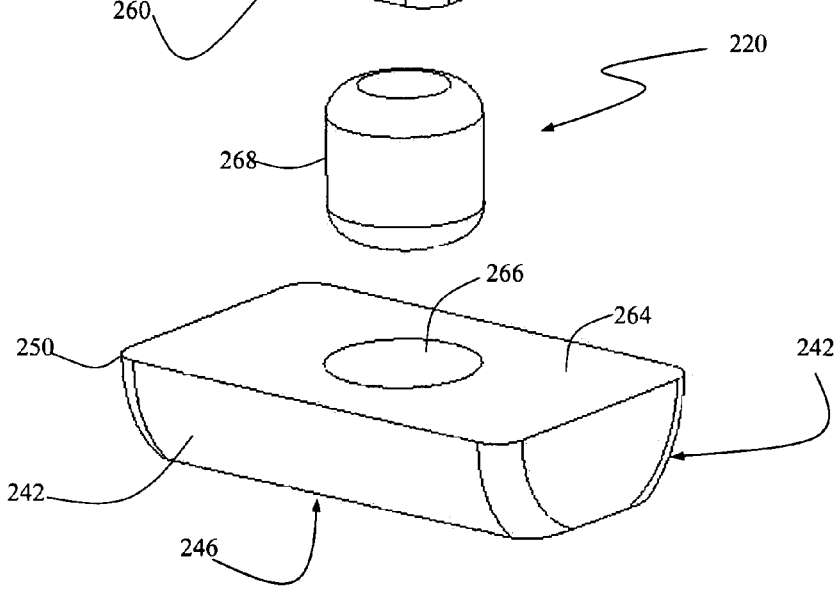
FIG. 20 is an exploded perspective view of the intradiscal element of FIG. 19.

FIGS. 19-20 illustrate the intradiscal element 220 in greater detail. In a preferred embodiment described herein, the intradiscal element 220 includes a first intradiscal pivot 248 rotatably coupled to a second intradiscal pivot 250. The first intradiscal pivot 248 may include a pair of articular surfaces 240, a first generally planar surface 244, and a second generally planar surface 260. The functional relationships of articular surfaces 240 and the first generally planar surface 244 are described above and will not be repeated here. As shown in FIG. 19A, second generally planar surface 260 may contain an aperture 262 located in a generally central region of the surface 260, and is dimensioned to interact with the second generally planar surface 264 of the second intradiscal pivot 250. Second intradiscal pivot 250 may include a pair of articular surfaces 242, a first generally planar surface 246, and a second generally planar surface 264. The functional relationships of articular surfaces 242 and the first generally planar surface 246 are described above and will not be repeated here. Second generally planar surface 264 may contain an aperture 266 located in a generally central region of the surface 264, and is dimensioned to interact with the first generally planar surface 260 of the first intradiscal pivot 248. By way of example only, the rotational relationship between first and second intradiscal pivots 248, 250 may be accomplished by providing a connecting element 268 and a pair of apertures 262, 266. The connecting element 268 may be generally cylindrical in shape and dimensioned to interact with apertures 262, 266.

FIG. 19 best illustrates the aspect of rotation between the first and second intradiscal pivots 248, 250. The first and second intradiscal pivots 248, 250 may be initially oriented in any number of different manners, including but not limited to the generally perpendicular orientation shown. From this position, the first and second intradiscal pivots 248, 250 may be rotated about the Y-axis in the range $\partial 1$ of between 0 and 20 degrees in either direction from the Z-axis (within the plane of the generally planar surfaces 260, 264 of the first and second intradiscal pivots 248, 250). Thus, when fully assembled, rotational aspect of the TDR system 210 of the present invention allows the first anchor plate 212 to rotate relative to the second anchor plate 214 in the range of between 0 and 20 degrees in either direction about the Y-axis.

In addition to the rotational capability about the Y-axis, the first pair of articular surfaces 240 is dimensioned to articulate with the semi-cylindrical surfaces 232 of the first pair of intradiscal liners 216, while the second pair of articular surfaces 242 is dimensioned to articulate with the semi-cylindrical surfaces 238 of the second pair of intradiscal liners 218. In use, since the first pair of intradiscal liners 216 is embedded in the cutout region 224 of the first anchor plate 212, and the second pair of intradiscal liners 218 is embedded in the cutout region 226 of the second anchor plate 214, the first anchor plate 212 is enabled to rotate relative to the intradiscal element 220 about the Z-axis, and the second anchor plate 214 is enabled to rotate relative to the intradiscal element 220 about the X-axis. As noted above, this also enables the first anchor plate 212 to translate relative to the intradiscal element 220 in either direction along the Z-axis, and the second anchor plate 214 to translate relative to the intradiscal element 220 in either direction along the X-axis. In this fashion, the TDR system 210 of this first embodiment provides rotation along three distinct axes (X, Y, Z) and translation along two distinct axes (X and Z).

The intradiscal element 220 of the present invention may be constructed from any number of materials and/or compositions suitable for medical applications, including but not limited to metallic compositions or alloys (such as Co—Cr—Mo), ceramics (such as zirconia and/or alumina), polymers (such as ultra-high molecular weight polyethylene), and/or any combination thereof. Where beneficial and appropriate, the intradiscal element 220 may also be coated with any number of suitable compositions, such as zirconium oxide coating found in U.S. Pat. No. 5,037,438, the contents of which are hereby incorporated into this disclosure as if set forth in its entirety.

Figure 21:
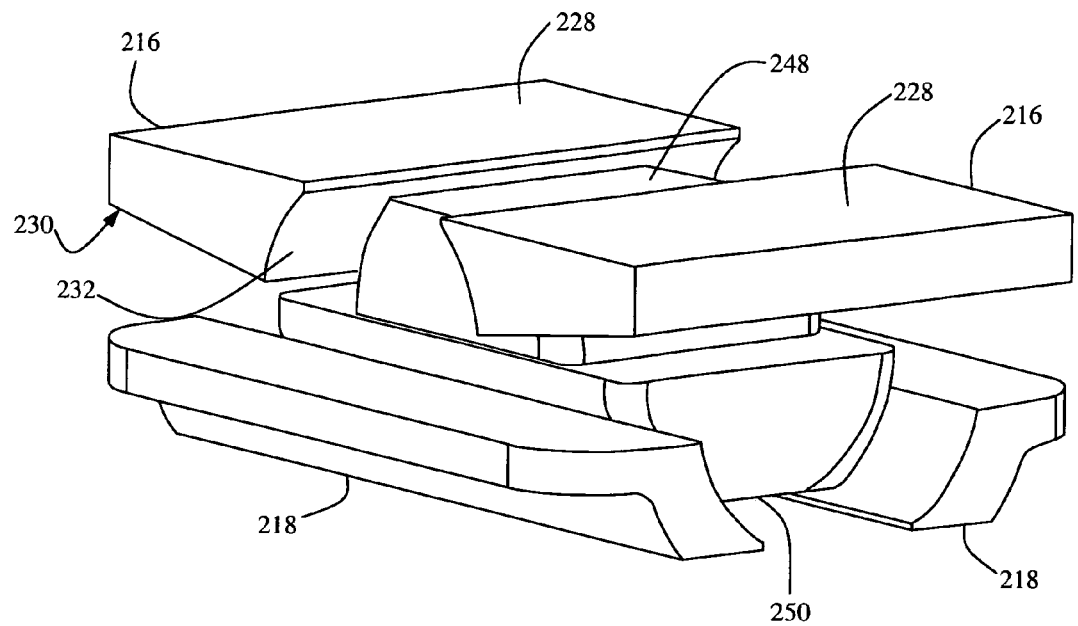
FIG. 21 is a perspective view of the intradiscal element of FIG. 19 in conjunction with two pairs of intradiscal liners forming part of the total disc replacement system of FIG. 14.
Figure 22:
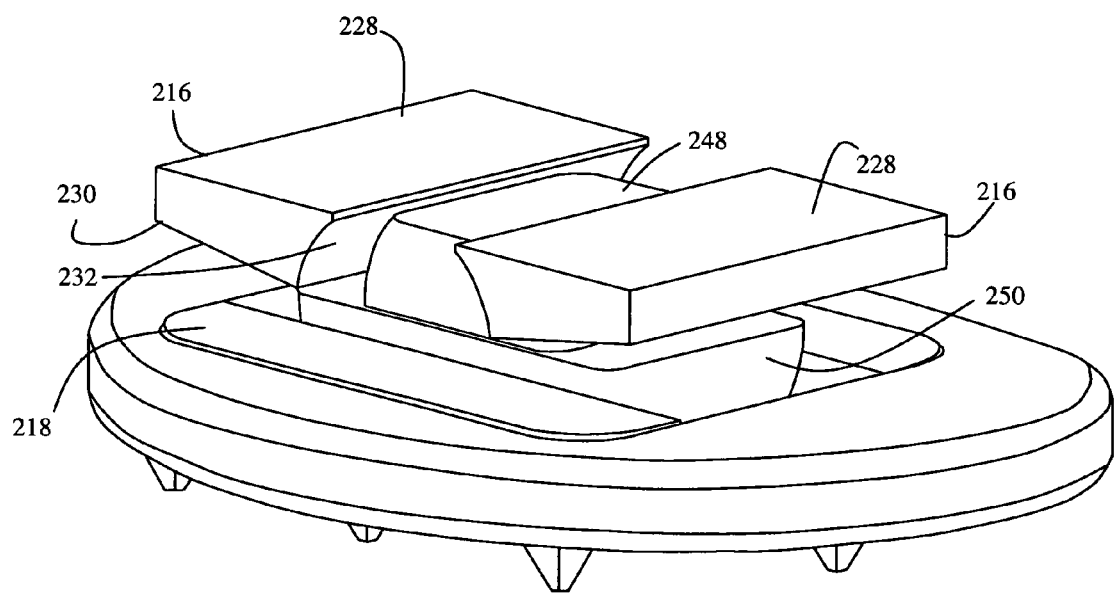
FIG. 22 is a perspective view of the total disc replacement system of FIG. 16 with a first anchor plate removed.

FIGS. 21-22 illustrate the first and second pairs of intradiscal liners 216, 218 in greater detail. The first pair of intradiscal liners 216 each have a first surface 228, a second generally planar surface 230, and a semi-cylindrical articular surface 232. The first surface 228 is dimensioned to fit into the cutout region 224 of the first anchor plate 212. Accordingly, the length of the first pair of intradiscal liners 216 traverses the width of the first anchor plate 212. As such, the length of the first pair of intradiscal liners 216 may not exceed, and is generally slightly less than, the width of the first anchor plate 212. The second generally planar surface 230 is dimensioned to interact with either the generally planar surface 264 of the second intradiscal pivot 250 or the generally angled surface 258 of the second anchor plate 214. As such, the second generally planar surface 230 functions to stop rotation of the first anchor plate about the Z-axis, as described above. The first pair of intradiscal liners 216 also forms a barrier between the intradiscal element 220 and the first anchor plate 212. This barrier serves to reduce friction between the first anchor plate 212 and intradiscal element 220, ultimately enhancing the durability of the TDR system 210 of the present invention.

The second pair of intradiscal liners 218 each have a first surface 234, a second generally planar surface 236, and a semi-cylindrical articular surface 238 dimensioned to articulate with the intradiscal element 220. The first surface 234 is dimensioned to fit into the cutout region 226 of the second anchor plate 214. Accordingly, the length of the second pair of intradiscal liners 218 traverses the length of the second anchor plate 214. As such, the length of the second pair of intradiscal liners 218 may not exceed, and is generally slightly less than, the length of the second anchor plate 214. The second generally planar surface 236 is dimensioned to interact with the generally angled surface 254 of the first anchor plate 212. As such, the second generally planar surface 236 functions to stop rotation of the first anchor plate about the X-axis, as described above. The second pair of intradiscal liners 218 also forms a barrier between the intradiscal element 220 and the second anchor plate 214. This barrier serves to reduce friction between the second anchor plate 214 and intradiscal element 220, ultimately enhancing the durability of the total disc replacement system 210.

The first and second pairs of intradiscal liners 216, 218 of the present invention may be constructed from any number of materials and/or compositions suitable for medical applications, including but not limited to metallic compositions or alloys (such as Co—Cr—Mo), ceramics (such as zirconia and/or alumina), polymers (such as ultra-high molecular weight polyethylene), and/or any combination thereof. Where beneficial and appropriate, the first and second pairs of intradiscal liners 216, 218 may also be coated with any number of suitable compositions, such as zirconium oxide coating found in U.S. Pat. No. 5,037,438, mentioned above. The first and second pairs of intradiscal liners 216, 218 may be secured to the recessed regions 224, 226 of the first and second anchor plates 212, 214 by any suitable method or material, including but not limited to biocompatible adhesive substances, brazing, and the like.

The TDR systems of the present invention may be provided with various modifications without departing from the scope of the invention. For example, the semi-cylindrical articular surfaces of the first and/or second anchor plates may be generally convex in addition to the generally concave configuration shown. In similar fashion, the generally arcuate cross-sections of the first and/or second articular surfaces of the intradiscal element may be generally concave in addition to the generally convex configuration shown. Moreover, the intradiscal element may be prevented from translating relative to the first and/or second anchor plates in any suitable fashion, such as by equipping the either or both of the anchor plates and/or the intradiscal element with a structure (e.g. a wall member extending from the anchor plate) or a stop along the length of the first and/or second semi-cylindrical articular surfaces.

It should be noted with particularity that the intradiscal element may take any number of forms without departing from the scope of the invention, provided it has a first articular surface and a second articular surface each having a generally arcuate cross-section. That is, in addition to the "dual mating semi-cylinders" configuration described above (with the first generally semi-cylindrical intradiscal element rotatably coupled to the second generally semi-cylindrical intradiscal element), the intradiscal element may be provided as a generally spherical configuration (of unitary or multi-component construction with the constituent components fused together or rotatable relative to one another), a "dual fixed semi-cylinder" configuration (wherein the first and second intradiscal elements are provided as a single element of unitary construction or multi-component construction with the constituent components fused or otherwise locked together), or any combination of the foregoing (e.g. with a semi-cylinder portion rotatably or fixedly coupled to a dome-shaped portion). In each instance, the language "first articular surface and a second articular surface, with each having a generally arcuate cross-section" shall include, but not necessarily be limited to, any or all of these variations.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A disc replacement system for use in the spine, comprising:
   a first anchor plate having a first surface for engaging a first vertebra and a second surface including a cutout region;
   a second anchor plate having a first surface for engaging with a second vertebra and a second surface including a cutout region;
   a first pair of intradiscal liners having a first surface for engaging with said cutout region of said first anchor plate and a second surface including a semi-cylindrical articular surface;
   a second pair of intradiscal liners having a first surface for engaging with said cutout region of said second anchor plate and a second surface including a semi-cylindrical articular surface; and
   an intradiscal element including a first pair of articular surfaces having generally arcuate cross-sections for articulating with said semi-cylindrical articular surface of said first pair of intradiscal liners and a first generally planar surface for engaging said cutout region of said first anchor plate, and a second pair of articular surfaces having generally arcuate cross-sections for articulating with said semi-cylindrical articular surface of said second pair of intradiscal liners and a second generally planar surface for engaging said cutout region of said second anchor plate.

2. The disc replacement system of claim 1, wherein said semi-cylindrical articular surface of at least one of said first and second pairs of intradiscal liners is at least one of generally concave and generally convex.

3. The disc replacement system of claim 1, wherein at least one of said generally arcuate cross-sections of said first and second pairs of articular surfaces of said intradiscal element is at least one of generally concave and generally convex.

4. The disc replacement system of claim 1, wherein at least one of said second surfaces of said first and second anchor plates includes a ramped portion to facilitate the introduction of said intradiscal element into articulating engagement with said semi-cylindrical articular surfaces of said first and second pairs of intradiscal liners.

5. The disc replacement system of claim 1, wherein at least one of said first and second anchor plates includes at least one endcap to prevent translation of at least one of said first and second pairs of intradiscal liners.

6. The disc replacement system of claim 1, wherein said first and second pairs of intradiscal liners are prevented from translating relative to said respective first and second anchor plates by at least one of a biocompatible adhesive substance and a brazing process.

7. The disc replacement system of claim 1, wherein said first anchor plate includes at least one anti-migration feature extending from said first surface for anchoring into said first vertebra and said second anchor plate includes at least one anti-migration feature extending from said first surface for anchoring into said second vertebra.

8. The disc replacement system of claim 7, wherein said anti-migration feature comprises a protrusion having a generally triangular cross-section.

9. The disc replacement system of claim 1, wherein at least one of said first anchor plate and said second anchor plate is at least one of generally rectangular and generally cylindrical in shape.

10. The disc replacement system of claim 9, wherein said first anchor plate has a generally rectangular shape including a length in the range of 15 mm and 40 mm and a width of less than 25 mm and said second anchor plate has a generally rectangular shape including a length in the range of 15 mm and 40 mm and a width of less than 25 mm.

11. The disc replacement system of claim 1, wherein said first and second anchor plates are configured such that they may be advanced through a minimal access surgical corridor.

12. The disc replacement system of claim 1, wherein said first and second anchor plates are configured such that they may be introduced in a generally lateral approach relative to said first and second vertebrae.

13. The disc replacement system of claim 12, wherein said first and second anchor plates are configured such that they may be introduced in a generally anterior approach relative to the first and second vertebrae.

14. The disc replacement system of claim 1, wherein said intradiscal element is generally spherical.

15. The disc replacement system of claim 1, wherein said intradiscal element comprises at least one of a single generally spherical member and at least two semi-spherical members coupled together.

16. The disc replacement system of claim 1, wherein said intradiscal element includes at least one generally semi-cylindrical articular surface for articulating with at least one of said semi-cylindrical articular surface of said first pair of intradiscal liners and said second pair of intradiscal liners.

17. The disc replacement system of claim 16, wherein said intradiscal element is a unitary member.

18. The disc replacement system of claim 16, wherein said intradiscal element comprises a first intradiscal element rotatably coupled to a second intradiscal element.

19. The disc replacement system of claim 18, wherein said first intradiscal element is rotatably coupled to said second intradiscal element via a post.

20. The disc replacement system of claim 1, wherein at least one of said first anchor plate, said second anchor plate, and said intradiscal element includes at least one lumen for engagement with an insertion tool.

21. The disc replacement system of claim 1, wherein at least one of said first anchor plate, said second anchor plate, said first pair of intradiscal liners, said second pair of intradiscal liners, and said intradiscal element is constructed from at least one of a metal, ceramic, polymer, and any combination of a metal, ceramic, and polymer.

* * * * *